United States Patent [19]
Hielscher et al.

[11] Patent Number: 6,011,626
[45] Date of Patent: *Jan. 4, 2000

[54] CHARACTERIZATION OF HIGHLY SCATTERING MEDIA BY MEASUREMENT OF DIFFUSELY BACKSCATTERED POLARIZED LIGHT

[75] Inventors: Andreas H. Hielscher, Brooklyn, N.Y.; Judith R. Mourant; Irving J. Bigio, both of Los Alamos, N.Mex.

[73] Assignee: The Regents of the University of California, Los Alamos, N.Mex.

[*] Notice: This patent issued on a continued prosecution application filed under 37 CFR 1.53(d), and is subject to the twenty year patent term provisions of 35 U.S.C. 154(a)(2).

[21] Appl. No.: 09/045,258

[22] Filed: Mar. 20, 1998

Related U.S. Application Data

[60] Provisional application No. 60/039,370, Mar. 20, 1997.

[51] Int. Cl.[7] .................................................. G01J 4/00
[52] U.S. Cl. ........................... 356/367; 356/364; 356/369
[58] Field of Search .................................. 356/367, 364, 356/369

[56] References Cited

U.S. PATENT DOCUMENTS

| 2,824,488 | 2/1958  | Bridges et al. .......................... 356/367 |
| 4,884,886 | 12/1989 | Salzman et al. .                                  |
| 5,073,025 | 12/1991 | Brooks .................................... 356/367 |
| 5,608,526 | 3/1997  | Piwonka-Corle et al. .............. 356/369 |

OTHER PUBLICATIONS

W. S. Bickel et al., "Application of Polarization Effects in Light Scattering: A New Biophysical Tool,"Proc. Natl. Acad. Sci. USA 73, No. 2, 486 (1976).

W. S. Bickel et al., "Polarized Light Scattering from Biological Systems: A Technique for Cell Differentiation," J. Biol. Phys. 9, 53 (1981).

K. M. Yoo et al., "Time Resolved Depolarization of Multiple Backscattered Light from Random Media," Phys. Lett. A 142, No. 8–9, 531 (1989).

R. R. Anderson, "Polarized Light Examination and Photography of the Skin," Archives of Dermatology 127, 1000 (1991).

S. L. Jacques et al., "Polarized Light Transmission Through Skin Yising Video Reflectometry Toward Optical Tomography of Superficial Tissue Layers," Lasers in Surgery: Advanced Characterization, Therapeutics, and Systems VI, R. R. Anderson, ed., Proc. Soc. Photo–Opt Instrum. Eng. 2671, 199 (1996).

(List continued on next page.)

*Primary Examiner*—Frank G. Font
*Assistant Examiner*—Reginald A. Ratliff
*Attorney, Agent, or Firm*—Samuel M. Freund

[57] ABSTRACT

An apparatus and method for recording spatially dependent intensity patterns of polarized light that is diffusely backscattered from highly scattering media are described. These intensity patterns can be used to differentiate different turbid media, such as polystyrene-sphere and biological-cell suspensions. Polarized light from a He-Ne laser ($\lambda$=543 nm) is focused onto the surface of the scattering medium, and a surface area of approximately 4×4 cm centered on the light input point is imaged through polarization analysis optics onto a CCD camera. A variety of intensity patterns may be observed by varying the polarization state of the incident laser light and changing the analyzer configuration to detect different polarization components of the backscattered light. Experimental results for polystyrene-sphere and Intralipid suspensions demonstrate that the radial and azimuthal variations of the observed pattern depend on the concentration, size, and anisotropy factor, g, of the particles constituting the scattering medium. Measurements performed on biological cell suspensions show that intensity patterns can be used to differentiate between suspensions of cancerous and noncancerous cells. Introduction of the Mueller-matrix for diffusely backscattered light, permits the selection of a subset of measurements which comprehensively describes the optical properties of backscattering media.

9 Claims, 23 Drawing Sheets

OTHER PUBLICATIONS

T. J. Farrell et al., "A Diffusion Theory Model of Spatially Resolved, Steady–State Diffuse Reflectance for the Noninvasive Determination of Tissue Optical Properties in vivo," Medical Physics 19, 879 (1992).

M. Dogariu et al., "Photon Pathlength Distribution from Polarized Backscattering in Random Media," Opt. Eng. 35, No. 8, 2234 (1996).

Andrea H. Hielscher et al., "Influence of Particle Size and Concentraiton on the Diffuse Backscattering of Polarized Light from Tissue Phantoms and Biological Cell Suspensions," Applied Optics 36, No. 1, 125 (1997).

C. F. Bohren et al, Absorption and Scattering of Light by Small Particles (John Wiley & Sons, New York, NY, 1983), p. 82.

B. Beauvoit et al., "Contribution of the Mitochondrial Compartment to the Optical Properties of the Rat Liver: A Theoretical and Practical Approach," Biophys. J. 67, 2501 (1994).

L. A. Kunz–Schugart et al., "Three–Dimensional Cell Culture Induces Novel Proliferative and Metabolic Alterations Associated with Oncogenic Transformation," Int. J. Cancer 66, 578 (1996).

Andreas Hielscher et al., "Diffuse Backscattering Mueller Matrices for Highly Scattering Media," Optics Express 1, 441 (1997).

W. S. Bickel et al., "Stokes Vectors, Mueller Matrices, and Polarized Scattered Light," Am. J. Phys. 53, No. 5, 468 (1985).

S. L. Jacques et al., "Video Reflectometry to Specify Optical Properties of Tissue in vivo," in Medical Optical Tomography: Functional Imaging and Monitoring, G. Mueller et al., eds., vol. ISII of SPIE Institute Series (Society of Photo-–Optical Instrumentation Engineers, Benningham, WA, 1992) p. 211.

A. Kienle et al., "Spatially Resolved Absolute Diffuse Reflectance Measurements for Noninvasive Determination of the Optical Scattering and Absorption Coefficients of Biological Tissue," Appl. Opt. 35, No. 13, 2304 (1996).

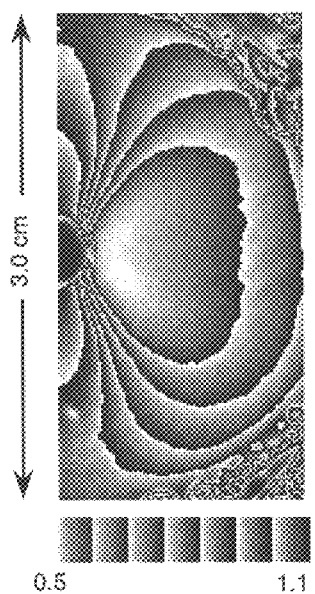 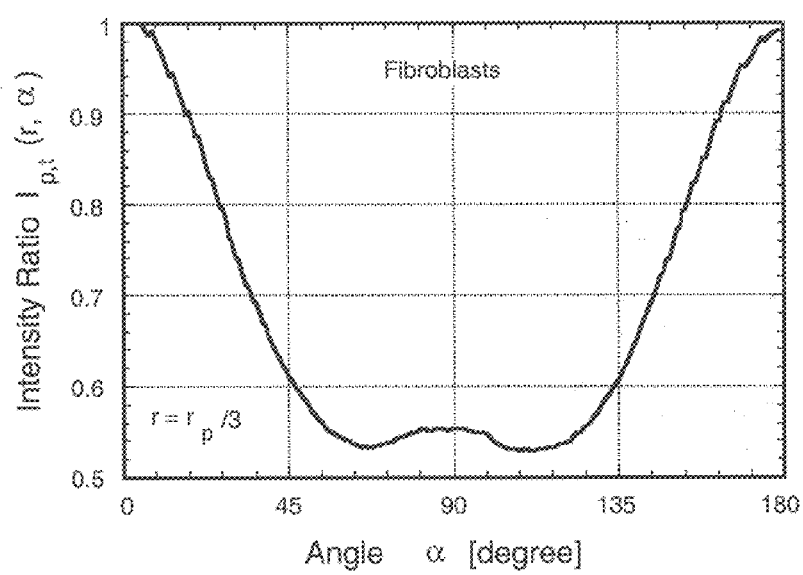
Fig. 14a          Fig. 14b

CHARACTERIZATION OF HIGHLY SCATTERING MEDIA BY MEASUREMENT OF DIFFUSELY BACKSCATTERED POLARIZED LIGHT

This application claims benefit of Provisional Appln. 60/039,370 filed Mar. 20, 1997.

The present invention relates generally to the use of polarization effects in light scattered from samples to yield information about these samples and, more particularly, to the use of spatially dependent intensity patterns of polarized light that is diffusely backscattered from highly scattering media to differentiate turbid media. This invention was made with government support under Contract No. W-7405-ENG-36 awarded by the U.S. Department of Energy to The Regents of The University of California. The government has certain rights in the invention.

FIELD OF THE INVENTION

BACKGROUND OF THE INVENTION

Polarization effects in scattered light are known to provide useful information about biological material. See, e.g., W. S. Bickel et al., "Application of Polarization Effects in Light Scattering: A New Biophysical Tool," Proc. Natl. Acad. Sci. USA 73, 486 (1976), where the angular distribution of components of the scattering matrix measured for scattering angles between 3° and 165° of polarized light were affected by suspensions of Bacillus Subtilis. The use of polarized-light scattering for biological cell differentiation was also demonstrated by Bickel et al. and by Salzman et al. See, e.g., W. S. Bickel et al., "Polarized Light Scattering from Biological Systems: A Technique for Cell Differentiation," J. Biol. Phys. 9, 53 (1981), and U.S. Pat. No. 4,884,886 for "Biological Particle Identification Apparatus", which issued to Gary C. Salzman et al. on Dec. 5, 1989.

The above-mentioned applications of polarized light require measurement of polarized irradiance over a range of forward scattering angles (between 0° and 180°), and are the result of single scattering events. However, there are many biomedical applications where the properties of backward-scattered light are of interest. For example, only backscattered light is available in endoscopic procedures that are used to diagnose tissues. Time-resolved measurements of the depolarization of multiple backscattered light from turbid media have been performed by Yoo and Alfano. See, e.g., K. M. Yoo et al., "Time Resolved Depolarization of Multiple Backscattered Light from Random Media," Phys. Lett. A 142, 531 (1989). In these experiments, 5-fs laser pulses, which were linearly polarized and collimated to a diameter of 5 mm, were directed onto latex-bead suspensions. The backscattered light within the beam area was collected and recorded as a function of time. It was observed that the depolarization varies with particle size and concentration and an estimate that approximately 20 scattering events are necessary to completely depolarize the light was proffered. Linearly polarized light has also been used to illuminate the skin of patients over a broad area. See, e.g., R. R. Anderson, "Polarized-Light Examination and Photography of the Skin," Archives of Dermatology 127, 1000 (1991), where viewing the skin through another linear polarizer permitted the reflectance from the skin surface (which preserves the plane of polarization) to be distinguished. The light backscattered from within the tissue, by contrast, is more likely to undergo a change in the plane of polarization or become depolarized.

Recently, Wang et al. and Jacques et al. reported azimuthal variations of intensity in the diffuse-backscattered, linearly polarized light around the light input point when viewed through a polarizing filter. See, e.g., S. L. Jacques et al., "Polarized Light Transmission Through Skin Using Video Reflectometry Toward Optical Tomography of Superficial Tissue Layers," Lasers in Surgery: Advanced Characterization, Therapeutics, and Systems VI, R. R. Anderson, ed., Proc. Soc. Photo-Opt. Instrum. Eng. 2671, 199 (1996). They found that these azimuthal variations vanished at approximately 2 transport mean-free-paths $(mfp'=1/[\mu_s(1-g)]=1/\mu_s')$ from the initial laser spot. For larger distances, r, an exponential decay in the light intensity is observed comparable to the case when no polarizers are used. See, e.g., T. J. Farrell et al., "A Diffusion Theory Model of Spatially Resolved, Steady-State Diffuse Reflectance for the Noninvasive Determination of Tissue Optical Properties in vivo," Medical Physics 19, 879 (1992). Dogariu and Asakura used the azimuthal intensity variations in the polarized, backscattered light for the determination of the average photon pathlength in a scattering medium. See, e.g., M. Dogariu et al., "Photon Pathlength Distribution from Polarized Backscattering in Random Media," Opt. Eng. 35, 2234 (1996).

Accordingly, it is an object of the present invention to characterize biological tissue and biological suspensions and other turbid samples by analyzing diffuse, multiply scattered, polarized, continuous-wave light which has been backscattered from the samples after impinging on a small area thereof.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the apparatus of this invention for measuring diffuse backscattering of electromagnetic radiation from a medium may include: a source of electromagnetic radiation having a chosen wavelength; a first polarizer for receiving and for selectively polarizing the electromagnetic radiation; means for directing the polarized electromagnetic radiation into a small (less than $\approx 1/(10 \mu_s')^2 = (mfp'/10)^2$ as defined hereinabove) area of the medium approximately perpendicular to the surface of the medium; means for collecting multiply scattered electromagnetic radiation emerging from the medium in the vicinity (approximately $(10/\mu_s')^2 = (10 \text{ mfp}')^2$) of the area of incidence of the electromagnetic radiation onto the medium and in the opposite direction to the direction of the incident electromagnetic radiation; a mask for blocking specular reflection from the surface of the medium in the collected backward scattered electromagnetic radiation; a second polarizer for receiving and for selectively polarization analyzing the collected backward-scattered electromagnetic radiation; and means for receiving the polarization-analyzed, collected backward scattered electromagnetic radiation and simultaneously recording the spatial components of the intensity thereof.

Preferably, the electromagnetic radiation is in the visible region of the spectrum.

In another aspect of the present invention, in accordance with its objects and purposes, the method hereof for differentiating among samples of turbid media may include the steps of: generating polarized electromagnetic radiation having selective polarization and a chosen wavelength; directing the polarized electromagnetic radiation into a small area of the turbid medium approximately perpendicular to the surface of the medium; collecting multiply scattered electromagnetic radiation emerging from the medium in the vicinity of the area of incidence of the electromagnetic radiation onto the medium and in the opposite direction to the direction of the incident electromagnetic radiation; blocking specular reflection from the surface of the medium in the collected backward-scattered electromagnetic radiation; polarization analyzing the backward-scattered electromagnetic radiation; and simultaneously recording the spatially resolved components of the intensity of the backward scattered electromagnetic radiation for at least one combination of selected polarization and polarization analysis, whereby the recorded spatially resolved components of the intensity for different media are compared for at least one such combination.

Preferably, the generated electromagnetic radiation is in the visible region of the spectrum.

It is also preferred that the step of polarization analyzing the backward-scattered electromagnetic radiation includes the use of generalized Mueller matrix analysis.

Benefits and advantages of the present invention include the analysis of tissue samples for which only backscattered light is available when endoscopic procedures are employed.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings:

FIG. 2a is a schematic representation of the apparatus of the present invention for measuring diffuse-backscattered polarized light from samples, while

FIG. 14 shows the intensity ratio $I_{p,t}(r, \alpha)$ obtained from an M1 rat fibroblast-cell suspension with parallel polarizers: (a) two-dimensional image, (b) one-dimensional graph with radius fixed at $r=r_p/3$=0.68 cm. In both cases $0 \leq \alpha \leq 180°$.

DETAILED DESCRIPTION

Briefly, the present invention includes the measurement of the spatial intensity patterns of diffuse, backscattered polarized light from samples in order to characterize these samples. It is demonstrated that particle size, particle concentration, and scattering-anisotropy factor, g, affect the spatial pattern of backscattered light when viewed through a polarizer.

Figure 1:
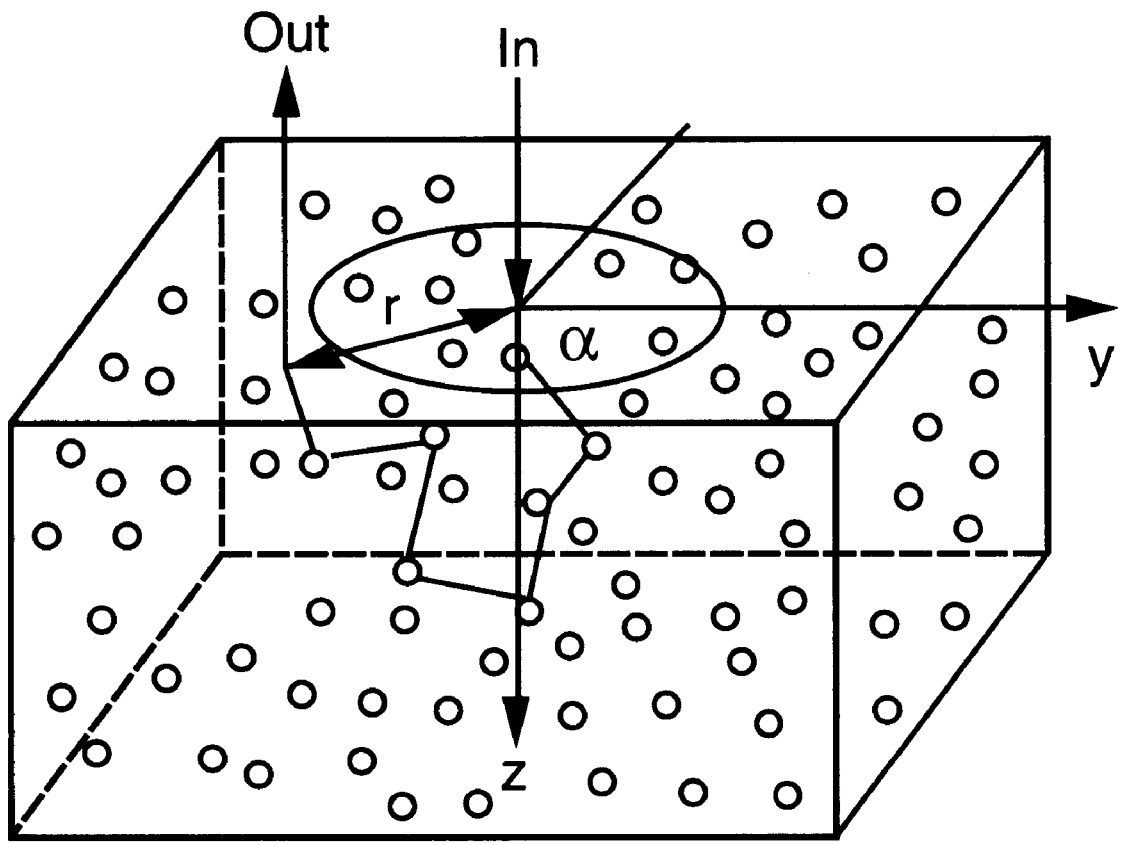
FIG. 1 is a schematic representation of the sample geometry for measurement of diffuse-backscattered polarized light of the present invention.
Figure 2A:
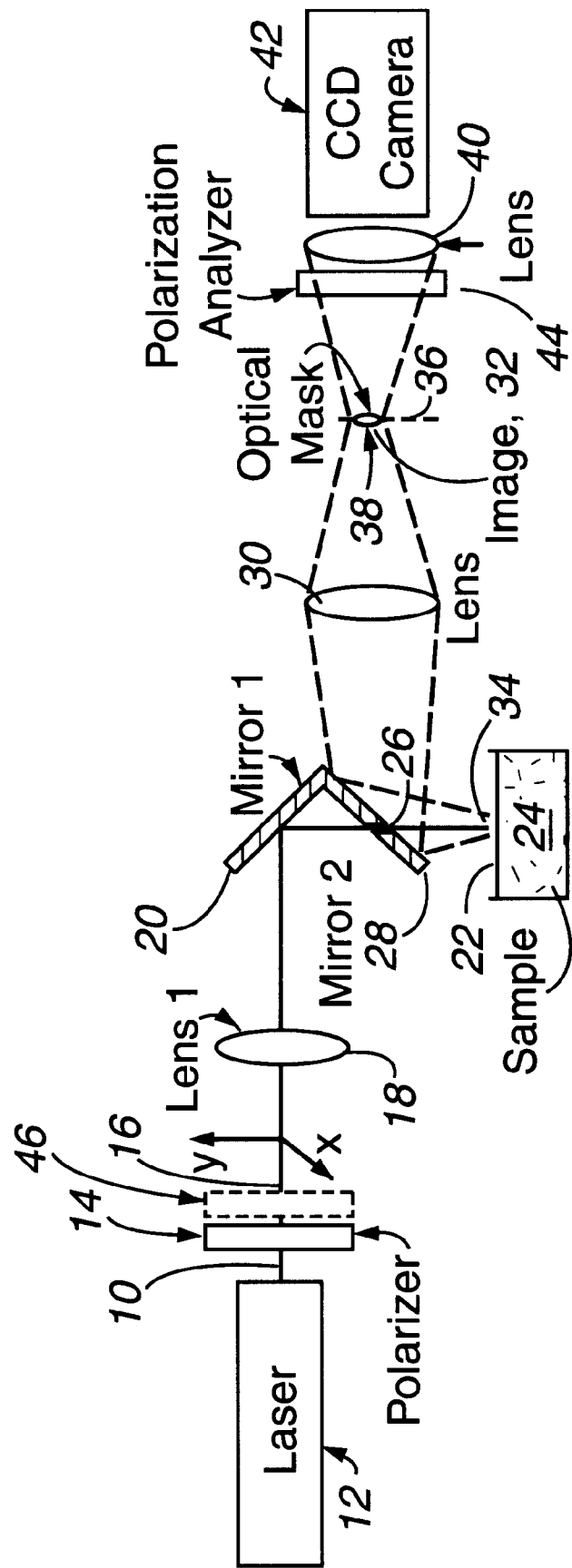
Figure 2B:
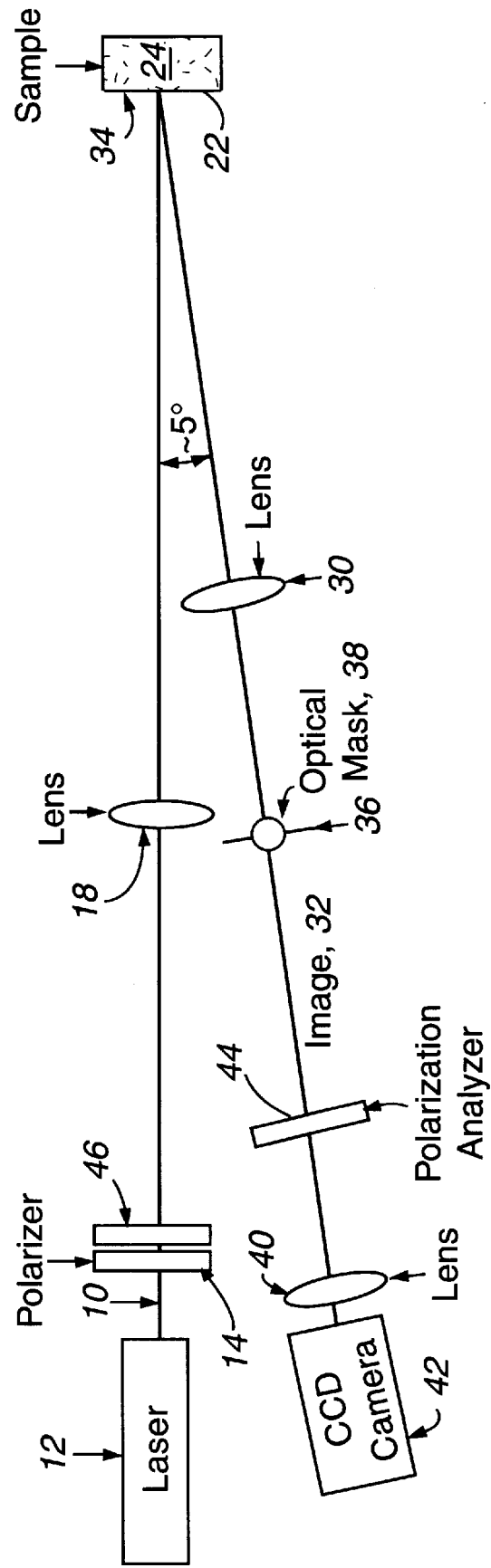
FIG. 2b is a second embodiment of the apparatus where light is directed onto the sample without the use of reflecting surfaces.

Reference will now be made in detail to the present preferred embodiments of the invention which are illustrated in the accompanying Figures. Similar or identical structure will be represented by identical callouts. Turning now to the drawings, FIG. 1 is a schematic representation of the sample geometry for the measurement of diffuse-backscattered polarized light. Instead of using a broad beam for sample illumination as is done in previous studies, polarized laser light is focused to a small spot (typically <500 mm in diameter) on the surface of the sample. This geometry is likely what will be used in endoscopic procedures where light is guided through an optical fiber to the area of interest. Diffusely backscattered light, then, is light that has been scattered multiple times inside the medium and escapes the medium, in a direction generally opposite to the direction of the impinging light, at a surface point that is given by a lateral distance, r, from the laser input point, and an angle, α, measured from the x-axis. FIG. 2a is a schematic representation of the apparatus of the present invention used for measuring the diffuse-backscattering of polarized light from a sample. Light, 10, from He-Ne laser, 12, having an output power of about 5 mW at a wavelength of λ=632.8 nm for linearly polarized measurements to be described hereinbelow and at a wavelength of λ=543 nm for the more general polarization measurements described hereinbelow, is directed into first polarizer, 14. Polarized light, 16, emerging from polarizer 14 is focused using first lens, 18, (f=15 cm) and first metallic mirror, 20, onto the surface, 22, of turbid medium, 24, through a hole, 26, in the center of second metallic mirror, 28. It should be mentioned that it is not necessary that the polarized light be incident exactly perpendicular to the surface of the medium. Small departures from normal incidence slightly distort the resulting patterns. Additionally, the use of nonmetallic mirrors alters the polarization applied to the electromagnetic radiation. Second lens, 30, (f=15 cm) generates an image, 32, of the surface area, 34, around the point of incidence of the light on surface 22 from light reflected from second mirror 28 in image plane, 36. Optical mask, 38, is located in the center of this image in order to block the strong specular reflection from the surface at the laser input point. Typically, mask diameters were about 1 mm; however, mask diameters up to 5 mm were employed. Image 32 including optical mask 38 was viewed using camera lens, 40 (55 mm, f/2.8), and cooled, intensified CCD camera, 42. The CCD chip had 575×384 pixels with a pixel size of 20×20 $\mu$m. The surface area 34 under observation around the laser entrance point could be varied from 0.5 cm×0.5 cm to 4 cm×4 cm, depending on the position of lenses 30 and 40. Second polarizer, 44, was placed in front of lens 40 to serve as a polarization analyzer. The dynamic range of the CCD camera was 12 bits. Images obtained using this apparatus are referred to as polarized-diffuse-backscattering (PDB) images. FIG. 2b shows a schematic representation of a second embodiment of the apparatus, where light is directed onto the sample without the use of reflecting surfaces (metallic mirrors 20 and 28). The 5° viewing angle of the backscattered electromagnetic radiation slightly distorts the resulting patterns.

Having generally described the invention, the following EXAMPLES provide additional detail. EXAMPLE 1 describes the results using the apparatus of FIG. 2 with linearly polarized light, while EXAMPLE 2 illustrates the more general case.

EXAMPLE 1

Aqueous polystyrene-sphere suspensions were employed as tissue phantoms containing a single type of scattering center. Spheres having chosen diameters (0.096, 0.204, 0.304, 0.497, 0.966, 2.04, 2.92, and 10.2 $\mu$m) were suspended in deionized water with trace amounts of surfactants. Concentrations of solids were varied by weight from 0.003% to 3.0%. The index of refraction of the spheres was 1.59 at 632.8 nm and the density was 1.05 g/ml. Intralipid in various concentrations was also used as a tissue phantom with scattering centers having known size distribution. Intralipid is a fat emulsion consisting of phospholipid micelles and water, which is used clinically as an intravenously administered nutrient. Because Intralipid has no strong absorption bands in the visible region of the electromagnetic spectrum, and because it is readily available and inexpensive, it is often used as a tissue-simulating phantom medium. The mean particle diameter is known to be 97 nm, and particle size ranges between 675 nm and 25 nm.

Yeast-cell suspensions were chosen as an example of biological cells, and were prepared according to the method described by Andreas H. Hielscher et al. See, e.g., Andreas H. Hielscher et al., "Influence of Particle Size and Concentration on the Diffuse Backscattering of Polarized Light from Tissue Phantoms and Biological Cell Suspensions," Applied Optics 36, 125 (1997). The optical properties of these cell suspensions for concentrations of 15–46 (mg dry weight)/ml were recently reported to lie in the range of $\mu_s'$=3–8.5 cm$^{-1}$ and $\mu_\alpha$=0.045–0.065 cm$^{-1}$. For several different suspensions, the mean cell diameter was between 4.7 and 5.5 $\mu$m, with standard deviations ranging from 3.5%–6.3%.

As an example of mammalian cells, measurements were also performed on rat fibroblast M1 cell suspensions. The fibroblast is the cell most commonly found in connective tissue. It is responsible for the synthesis of fibers and amorphous intercellular substances. Fibroblasts are rich in mitochondria, lipid droplets, Golgi complexes, and rough endoplasmic reticulum. Rat fibroblast M1 cells were prepared according to the method described in Hielscher et al., supra. Cells were counted using an electronic particle counter equipped with a system for recording the volume distribution of the particles. Only those particles within the cell volume distribution were counted, and the mean volume of the cell population was estimated as the mean of the volume distribution of >10$^4$ cells. The mean cell diameter for various samples was between 13 and 16 $\mu$m, with standard deviations ranging from 6.5% to 11%. Fibroblast and yeast cells in suspension tend to assume a spherical shape, which was confirmed with microscopic observation.

To quantify the surface images taken from the various scattering media, a spatial calibration was performed by the placement of a millimeter-resolution standard United States Air Force Optical Test Pattern 38710 on the surface of the sample. Under white-light illumination an image was acquired with the CCD camera and stored as reference. Dark measurements with a closed shutter in front of the CCD camera were taken to determine the background signal, which was to be subtracted from all images before further data processing. The response function of the CCD camera was determined by shining light into the camera and successively placing neutral-density filters in front of the camera until the signal level reached the dark level. This procedure was repeated for several values of the internal camera amplification, and the images were corrected accordingly.

Three types of images of the surface of the scattering medium surrounding the light input point were taken: (1) first and second linear polarizers removed ($I_t$); (2) first and second polarizers crossed with respect to each other ($I_x$); and (3) first and second polarizers parallel with respect to each other ($I_p$). The images taken with polarizers were divided point-by-point by the images taken without polarizers to yield the intensity ratios:

$$I_{p,t}(r,\alpha) = \frac{I_p(r,a)}{I_t(r,a)}, \qquad I_{x,t}(r,\alpha) = \frac{I_x(r,a)}{I_t(r,a)}. \tag{1a,b}$$

By normalizing against $I_t$, effects caused by the r-dependent exponential intensity decay are eliminated. This decay is typical in multiple-scattering media for point illumination by a continuos light source. Therefore, the chosen normalization ensures that only effects that are due to the linear polarization of the light are observed.

In order to eliminate noise arising from noisy sensors or electrical transmission errors which usually appears as discrete, isolated, strong pixel variations that are not spatially correlated, a 3×3 median filter was applied to the calculated images of the intensity ratios. The median filter used assigns the median value of the nine pixels of a 3×3 square to the center pixel and effectively eliminates discrete, isolated strong pixel variations. A spatial low-pass filter, which also assigns the mean value of the nine pixels of a 3×3 square to the center pixel, was used to smooth the data further. Finally, the contrast of the displayed images was enhanced by the application of a histogram equalization and a multibanded gray scale.

FIGS. 3(a) and 3(b) show two examples of measurements. The PDB images display intensities of diffuse-backscattered light for a surface area of 1.75 cm×1.75 cm, which images to 320×320 pixels on the CCD. The light is linearly polarized along the x axis and enters the medium in the center of all figures. This center is obscured by a circular mask which rejects the specular reflection of the laser spot from the surface of the medium. The line-like disturbance that enters the pictures from the left is caused by a 0.5-mm-diameter needle used to hold the mask. FIG. 3(a) is the result of a measurement on a yeast-cell suspension with the first and second polarizers crossed. FIG. 3(b) shows the same suspension with both polarizers removed. With no polarizers present the intensity is highest in the center around the mask and decays exponentially with distance from the center. There is no azimuthal dependence of the intensity. With crossed polarizers (FIG. 3(a)) a strong azimuthal dependence appears with maxima at ±45° and ±135°. This azimuthal dependence disappears at some distance from the center, after which the simple exponential radial dependence dominates. The result of a point-by-point division of FIG. 3(a) by FIG. 3(b), the intensity ratio $I_{x,t}(r, \alpha)$, is shown in FIG. 3(c). Instead of four maxima at ±45° and ±135°, minima with values smaller than 1 appear at 0° and 90°. Toward the edges of the image the ratio becomes 1. The azimuthal dependence in FIG. 3(a) disappears at approximately r=0.5 cm from the center, whereas in FIG. 3(c) the azimuthal dependence is clearly still visible at r=0.8 cm.

As will be described hereinbelow, the azimuthal and radial dependence of PDB patterns are influenced by the size, the anisotropy factor g and the concentration of the particles responsible for the scattering; therefore, patterns, such as that of FIG. 3(c), can be used to gain information about the scattering medium.

Polystyrene-sphere suspensions with spheres having known diameter, d, and concentration or number density, $N_s$, were used to quantify these effects. Mie theory was used to calculate the scattering phase function $p(\Omega,\Omega')$, which describes the probability that during a scattering event a photon with initial direction $\Omega'$ is scattered in the direction $\Omega$. See, e.g., C. F. Bohren et al., *Absorption and Scattering of Light by Small Particles* (John Wiley & Sons, New York, N.Y., 1983), p. 82. The anisotropy factor, g, may then be defined as $$g \equiv \int_{4\pi} \Omega \cdot \Omega' p(\Omega, \Omega') d\Omega'. \tag{2}$$

Furthermore, Mie theory was used to calculate the scattering cross section $C_s$ of the individual particles. Given the number density $N_s$, the scattering coefficient can be determined as $\mu_s = N_s C_s$. The inverse of $\mu_s$ gives the average distance between the two scattering events, also called the mfp. Finally, the reduced scattering coefficient $\mu_s' = (1-g)\mu_s$ may be calculated. The transport mfp (mfp') is defined as the inverse of $\mu_s'$.

Figure 3:
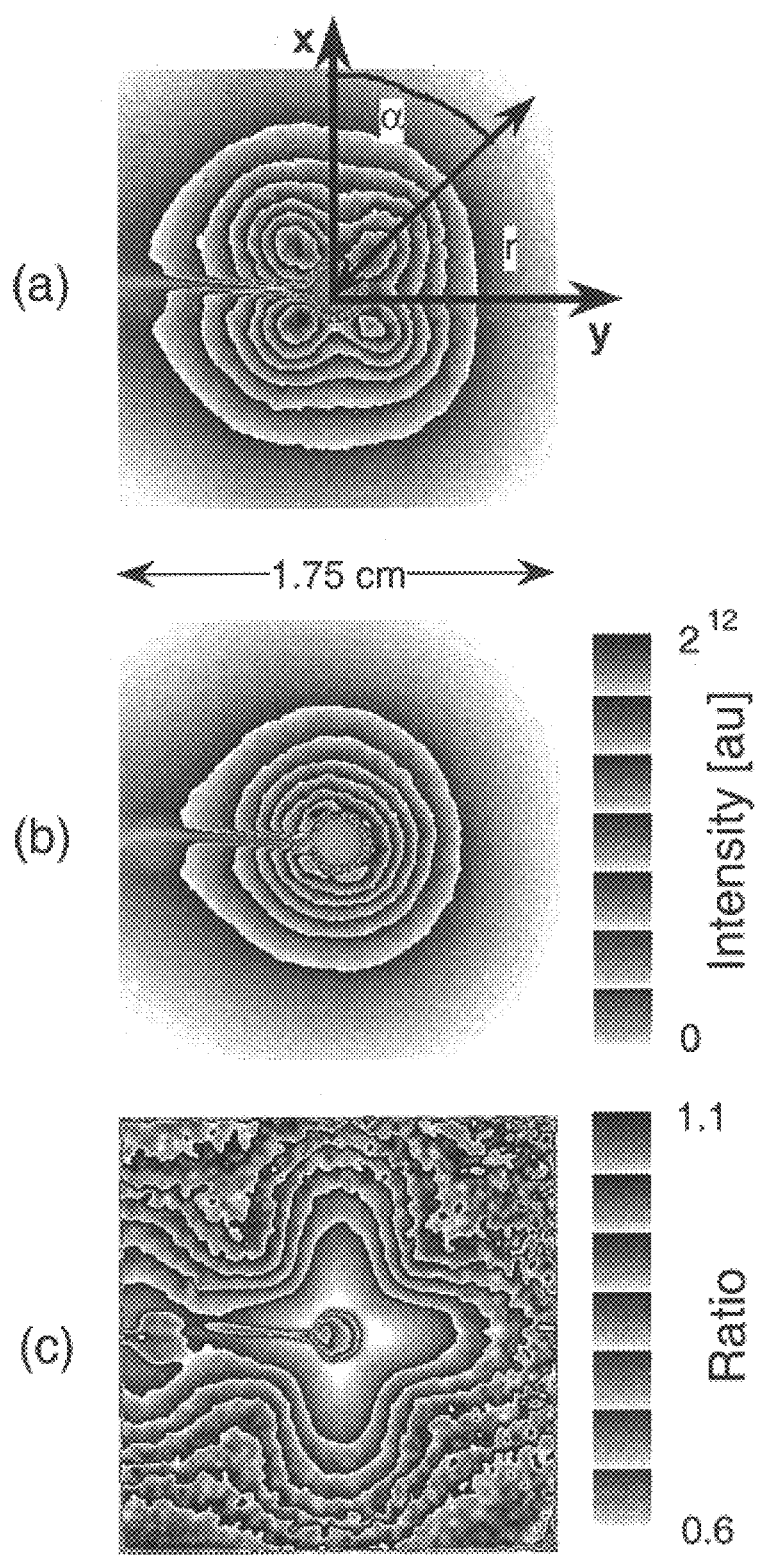
FIG. 3(a) is an image of the diffuse-backscattered intensity from a yeast cell suspension taken with crossed first and second polarizers.
FIG. 3(b) is an image of the diffuse-backscattered intensity from a yeast cell suspension taken without polarizers.
FIG. 3(c) is a point-by-point division of the image in FIG. 3(a) by the image in FIG. 3(b) and was additionally rendered by filter operations and contrast enhancement.
Figure 4:
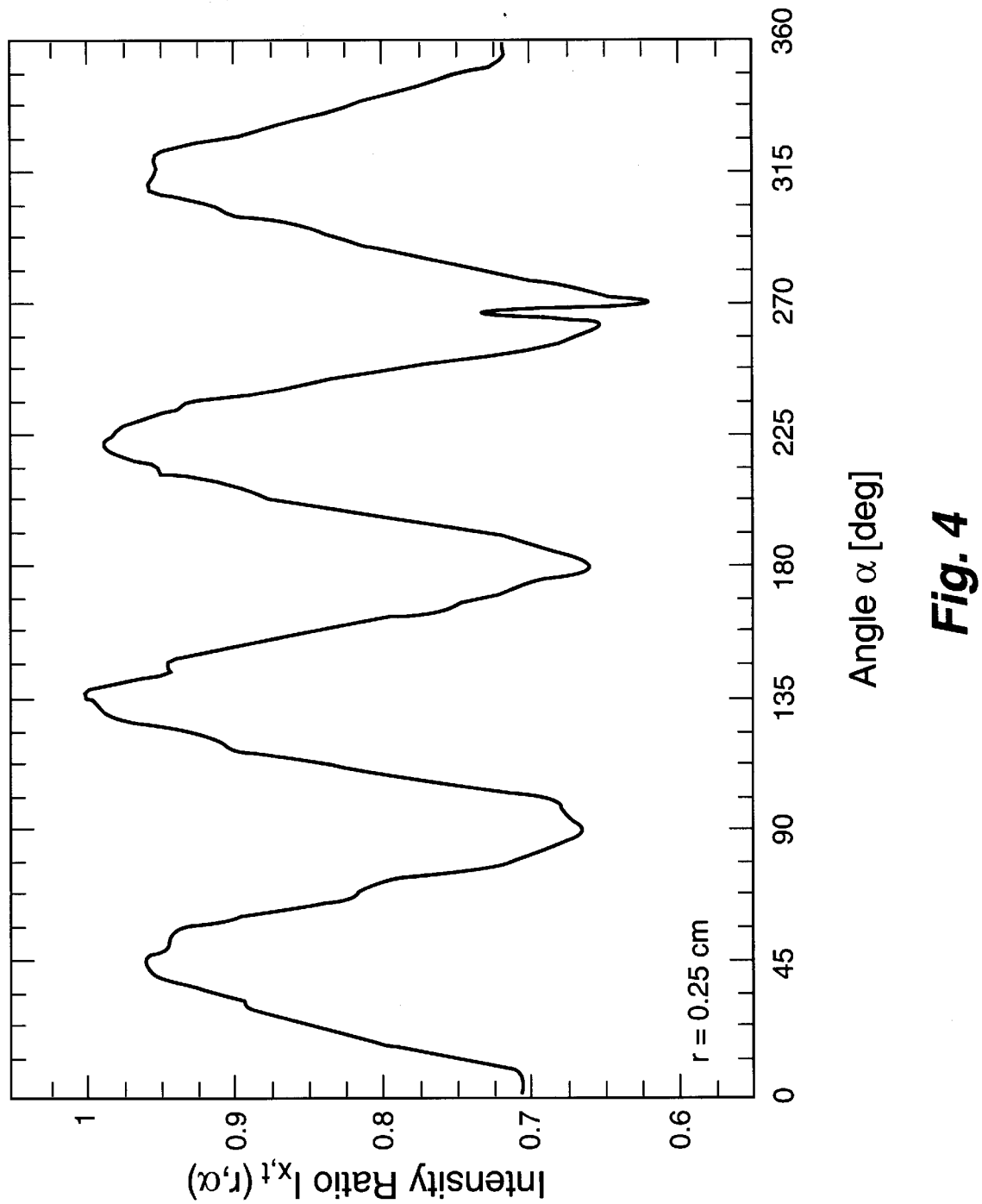
FIG. 4 shows values of the intensity ratio (FIG. 3(a)/FIG. 3(b)) on a circle with radius r=0.25 cm, centered around the light input point in the middle of FIG. 3(c).

The pattern size is determined by observing the azimuthal variations (angle α in FIG. 1) of the backscattered intensity ratio $I_{x,t}$ or $I_{p,t}$ at a radius r from the light input spot. In FIG. 4 this ratio is shown for a circle with radius r=0.25 cm centered in the middle of FIG. 3(c). The spike at 270° is caused by the holder of the optical mask and may be ignored. For this example the azimuthal variations are stronger than 30%. The radius at which these azimuthal variations become smaller than 5% is defined as the pattern size, $r_p$. This definition was chosen because the noise level of the patterns is approximately 5%. Other definitions (e.g., 2%, 10%, etc.) are possible and will not change the results.

Figure 5:
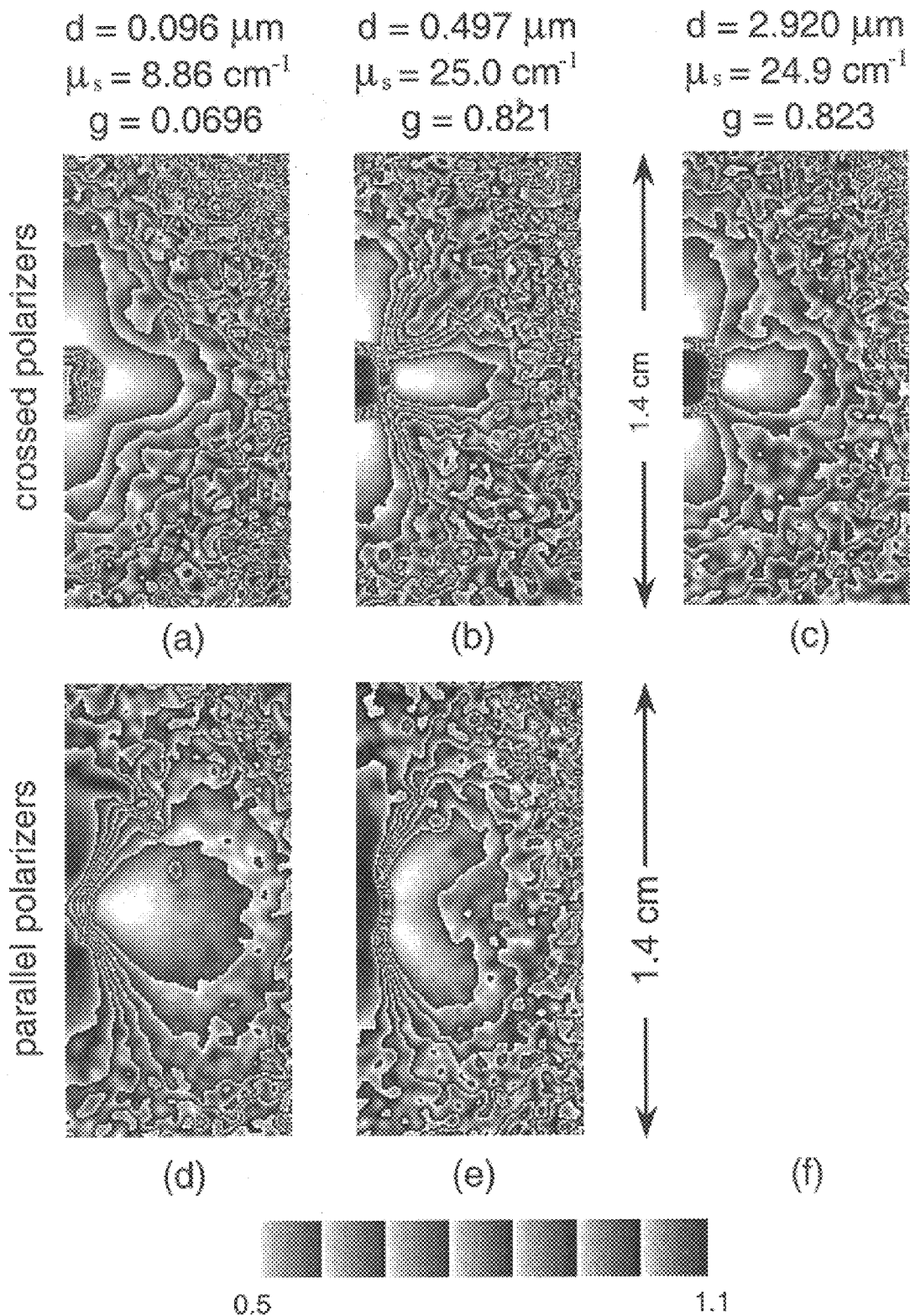
FIG. 5 shows two-dimensional intensity ratios $I_{x,t}(r,\alpha)$ and $I_{p,t}(r,\alpha)$ calculated from PDB images of polystyrene-sphere solutions with (a), (b), (c) crossed polarizers, (d),(e), (f) parallel polarizers. The column pairs [(a), (d)], [(b), (e)], and [(c), (f)] have the same sphere diameter d, scattering coefficient $\mu_s$, and anisotropy factor g, respectively.

It is now investigated how the diffuse-backscattered light is influenced by the particle size. FIG. 5 shows intensity ratio images from three suspensions that contain polystyrene spheres with different diameters. Instead of the whole images as in FIG. 3, only the right halves of the figures are shown because all the images are symmetric with respect to the x axes. The images, $I_{x,t}(r, \alpha)$ in FIGS. 5(a)–5(c) were obtained with crossed polarizers, whereas the images $I_{p,t}(r, \alpha)$ in FIGS. 5(d)–(f) were obtained with parallel polarizers. Compared with the wavelength of the He-Ne laser that was used in these experiments (632.8 nm), the diameters d of the spheres are several times smaller (FIGS. 5(a) and 5(d): d=0.096 μm with standard deviation, SD=0.0053 μm), similar (FIGS. 5(b) and 5(e): d=0.497 μm, SD=0.0056 μm), and several times larger (FIGS. 5(c) and 5(f): d=2.92 μm, SD=0.04 μm). Moreover, the suspensions of FIGS. (b), 5(e), 5(c) and 5(f) have approximately the same scattering coefficient $\mu_s$, 25.0 cm$^{-1}$ and 24.9 cm$^{-1}$, respectively, and similar anisotropy factors g, 0.821 and 0.823, respectively, at the He-Ne wavelength λ=632.8 nm.

The azimuthal structure in the case of crossed polarizers (FIGS. 5(a)–5(c)) does not have a strong dependence on the particle size. Although the shapes of the minima lobes differ slightly, the angles at which they occur are, in all three cases, the same at 0° and 90°. In the case of parallel polarizers (FIGS. 5(d)–5(f)), more pronounced differences in the azimuthal distributions can be observed. For the largest spheres (FIG. 5(f)), two minima can be found at 45° and 135° with respect to the polarization of the incoming light (FIG. 3).

The cross pattern appears to have been rotated by 45°, when compared with the pattern in FIG. 5(c). The sphere suspension with about the same $\mu_s$ and g but different particle size (FIG. 5(e)) displays a different pattern. Minima still occur at 45° and 135°; however, the minima are much broader and for small r extend also in the 90° direction to form a butterfly-like pattern. For the suspension with even smaller particles (FIG. 5(d)) this extension at 90° has become sufficiently strong that only one minimum is visible, and the cross structure disappears.

Figure 6:
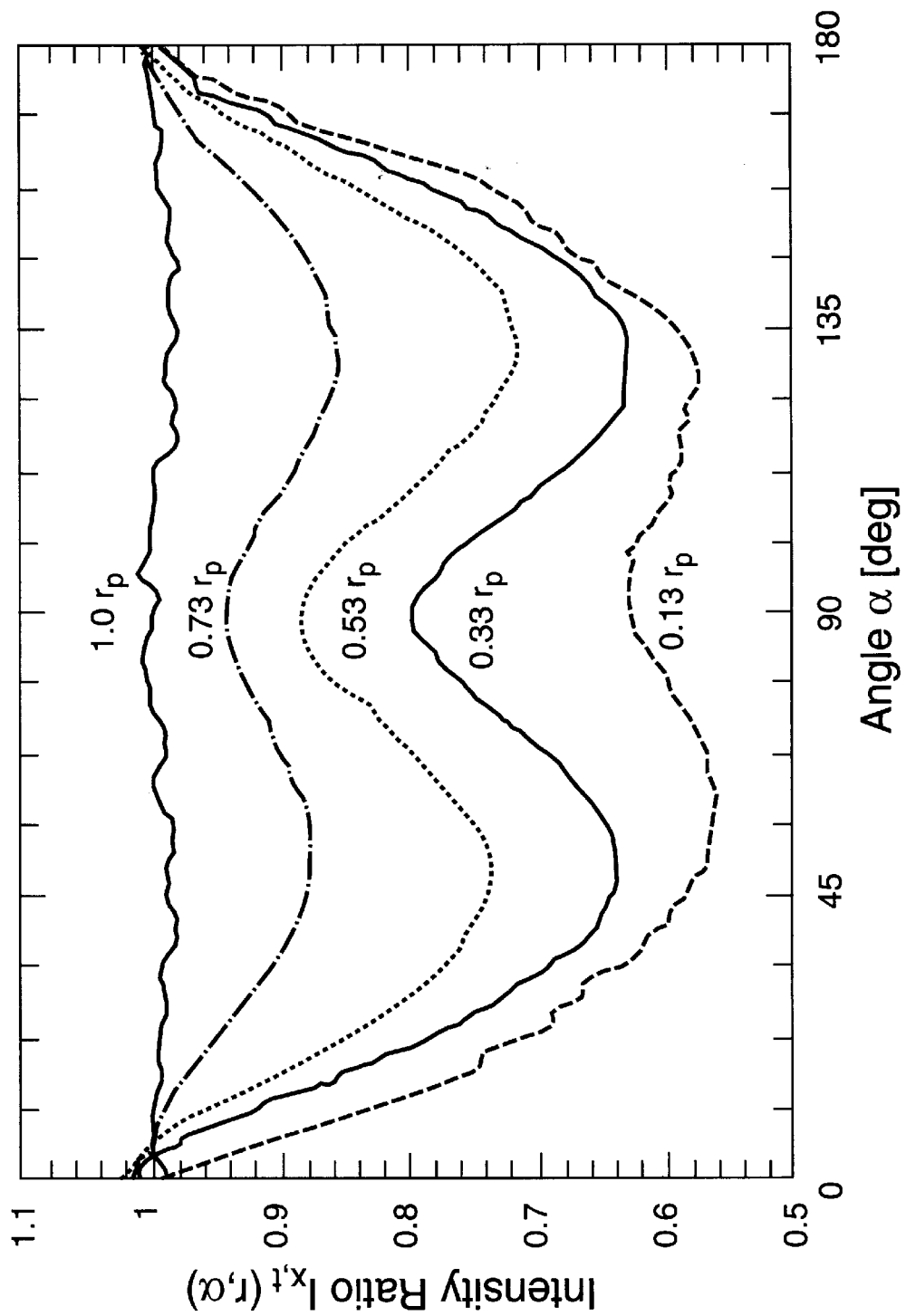
FIG. 6 shows intensity ratios $I_{p,t}(r,\alpha)$ as functions of azimuthal angle $\alpha$ for various radii $r \leq r_p$. Here the results of a polystyrene-sphere suspension with sphere diameter d=0.966 μm is shown.

Rather than a two-dimensional image of the sample surface around the light input point, FIG. 6 shows the intensity ratios for various fractions of the radius of the pattern size $r_p$ as a function of the azimuthal angle α. Here the results of a polystyrene-sphere suspension with sphere diameter d=0.966 μm (SD=0.6%) are shown. It can be seen that the difference in the intensity between 0° and 90° increases as the fraction decreases. This was observed for all particle sizes.

Figure 7:
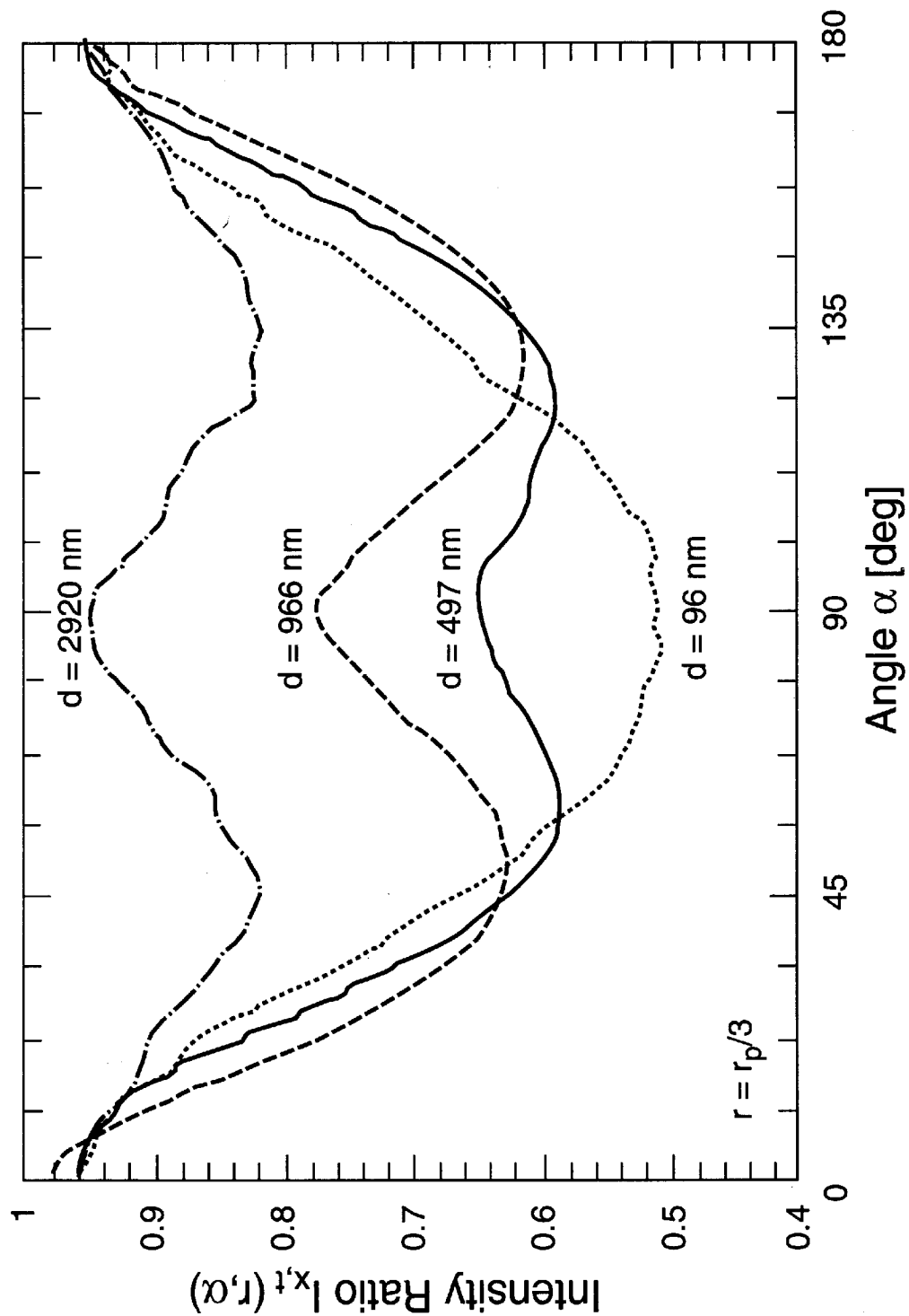
FIG. 7 shows intensity ratios $I_{p,t}(r,\alpha)$ of FIGS. 5(d)–5(f) and FIG. 6 for a fixed radius of $r=r_p/3$ as functions of the azimuthal angle $\alpha$.

FIG. 7 displays the intensity ratios of FIGS. 5(d)–5(f) and FIG. 6 for the fixed radius of r=$r_p$/3 as a function of the azimuthal angle, α. The radius $r_p$/3 was chosen because it was found that for smaller radii the distortions caused by the optical mask increase, whereas for larger radii, as shown in FIG. 6, the variations in the intensity ratios as a functions of angle decrease. FIG. 7 shows that for an increasing particle size the minimum at 90° becomes a local maxima and two new minima at 45° and 135° appear. This is true not only for r=$r_p$/3 but for all radii r<$r_p$.

Figure 8:
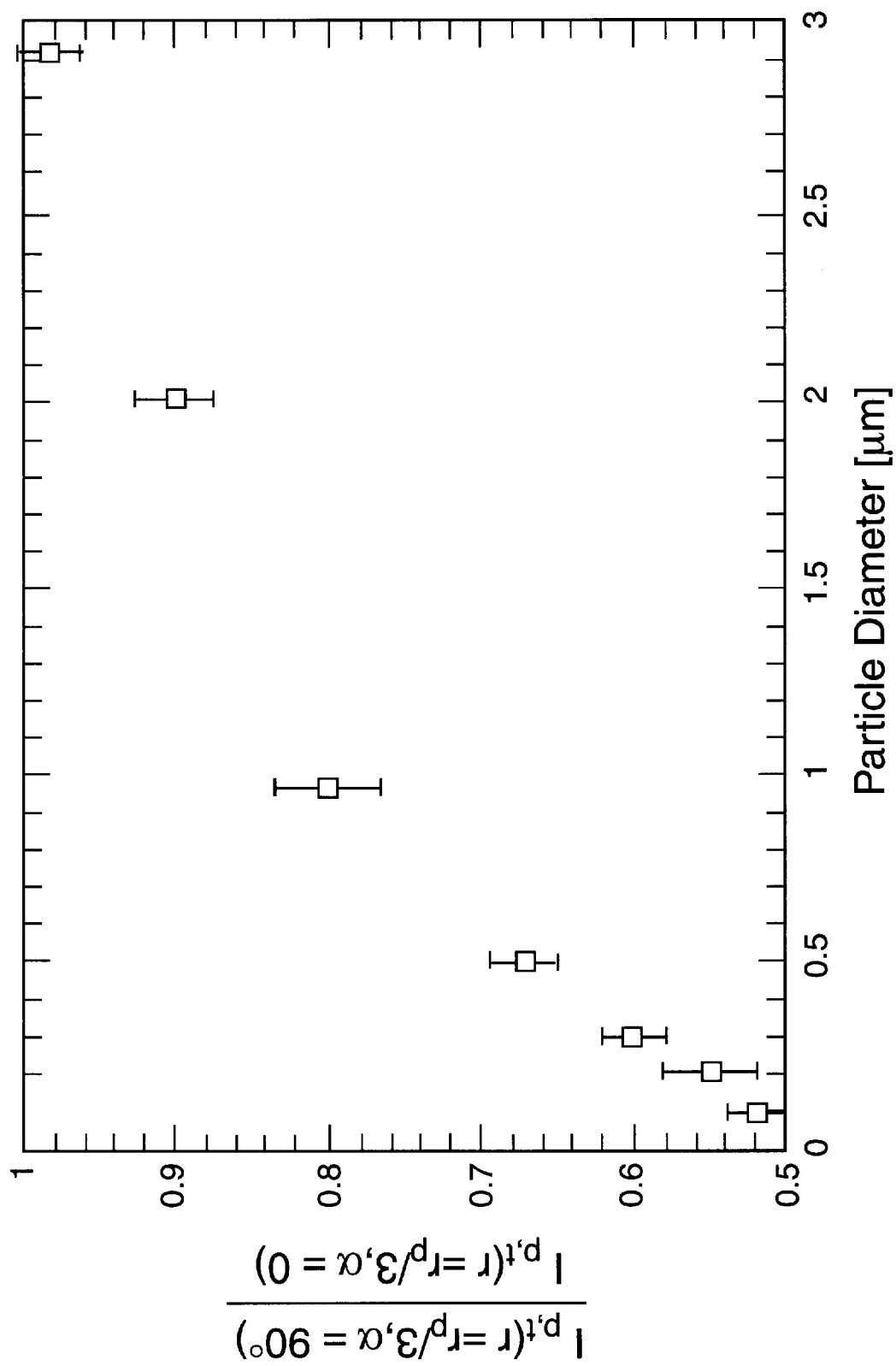
FIG. 8 shows the dependence of the ratio of $I_{p,t}(r=r_p/3, \alpha=90°)/I_{p,t}(r=r_p/3, \alpha=0°)$ on the particle diameter in polystyrene-sphere suspensions.

In general it can be concluded that the ratio of the intensities at 0° and 90°, for any given radius r<$r_p$, is related to the size of scattering particles in the suspension. In FIG. 8 the ratios of the intensities at 0° and 90° for seven polystyrene-sphere suspensions with different particle diameters are displayed. For particle size larger than 3 μm this ratio was 1. Again r=$r_p$/3 was chosen as the radius. If a larger radius is chosen, the curve is shifted up towards 1, whereas for smaller radii the curve shifts to lower values. Similarly, the curve will shift if the definition of the pattern size $r_p$ is changed.

Figure 9:
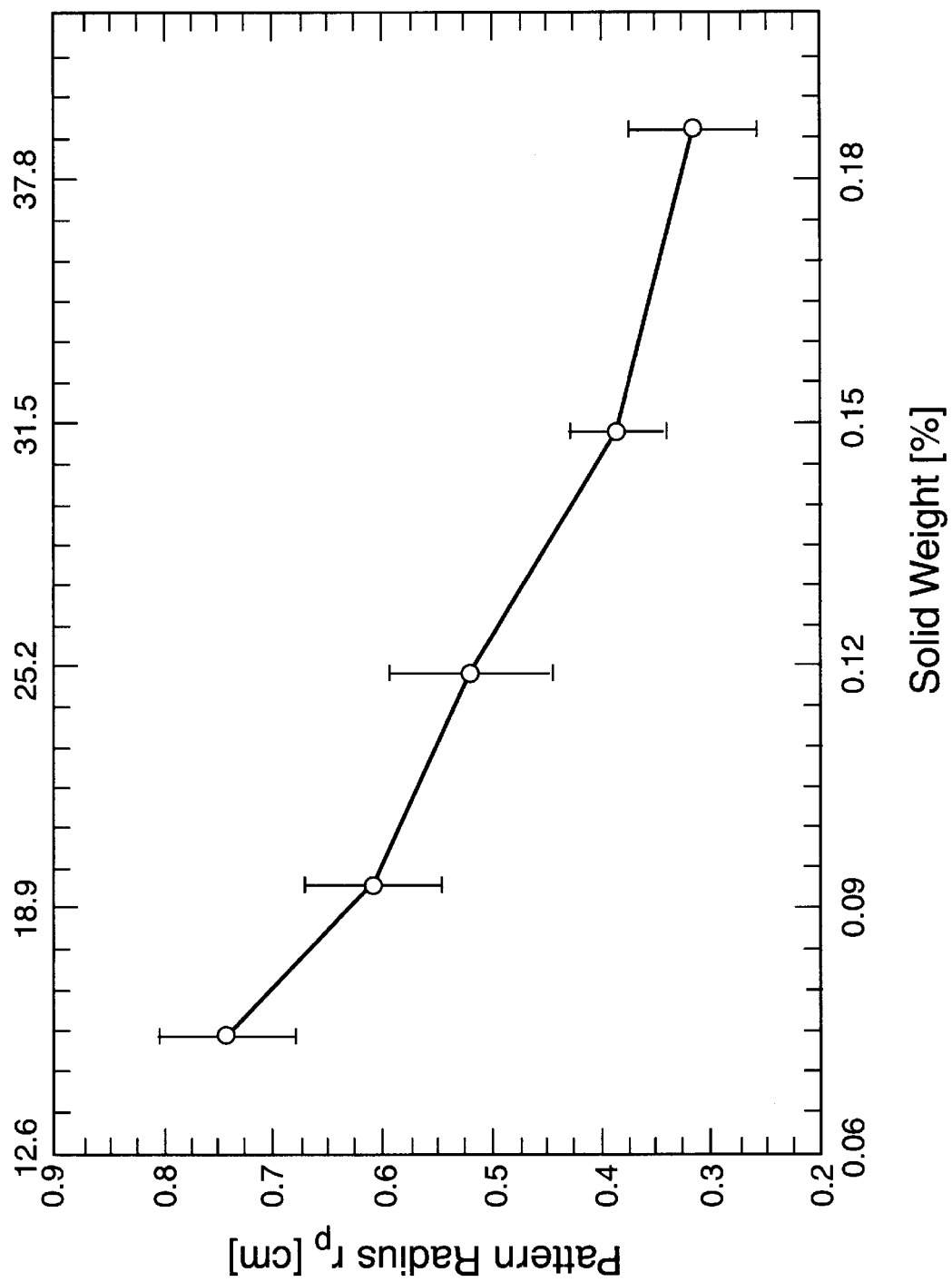
FIG. 9 shows a pattern radius $r_{xp}$ for the case of crossed polarizers for polystyrene-sphere suspension with a particle diameter of d=0.497 μm as a function of particle concentration.

In all experiments it was observed that changing the concentration of the sphere suspensions, thereby changing the macroscopic scattering coefficient $\mu_s$, does not change the azimuthal dependence. However, the particle concentrations affect the pattern size, $r_p$. Increasing the concentration of particles in the solution by a factor of n led to a decrease of the pattern radius, $r_p$, by a factor of n. An example is shown in FIG. 9. Here, the pattern radius for the case of crossed polarizers was determined for polystyrene-sphere suspensions with a particle diameter of d=0.497 μm. The concentration was varied from 0.075% to 0.186% solid weight of polystyrene spheres. The corresponding scattering coefficients $\mu_s$ were calculated from Mie theory and are provided in the scale on the top of the graph. Doubling the concentration from 0.093% to 0.186% approximately halves the radius $r_p$ from 0.61 cm to 0.31 cm.

Figure 10:
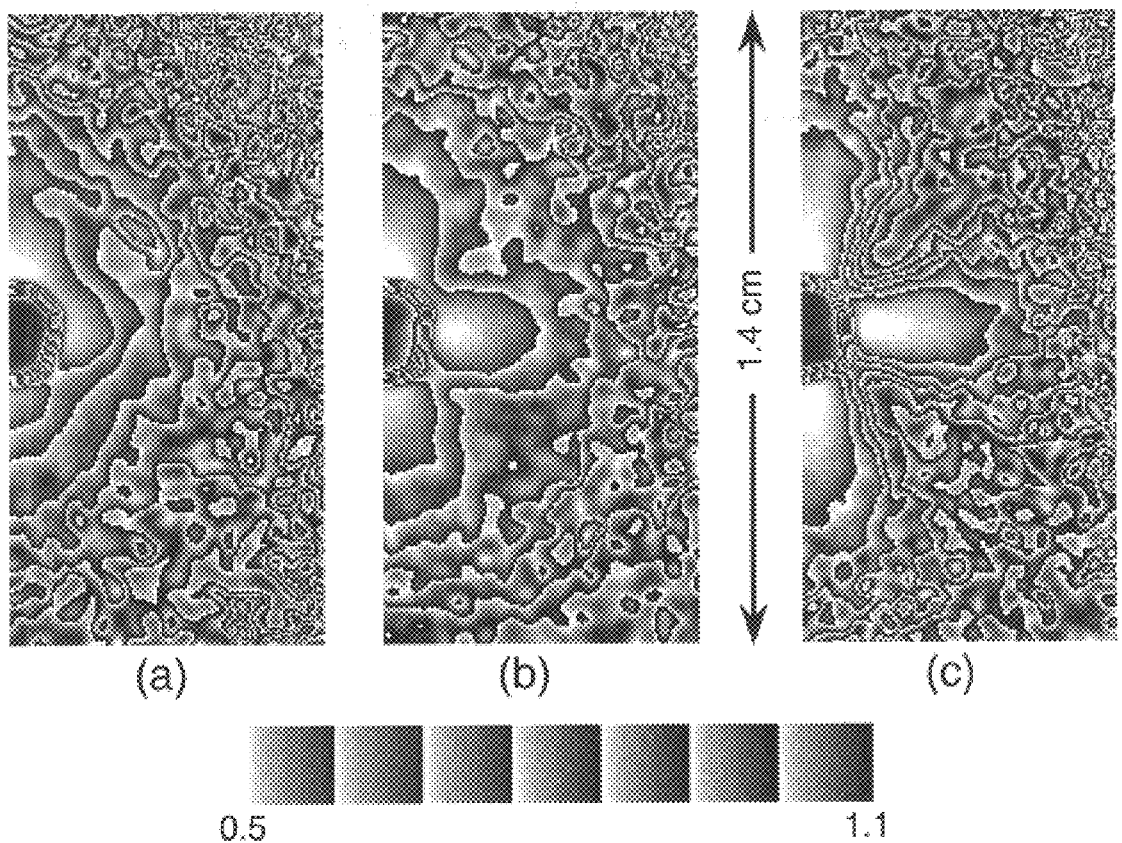
FIG. 10 shows two-dimensional intensity ratios $I_{x,t}(r,\alpha)$ as calculated from images of a polystyrene-sphere suspension with crossed polarizers: (a) g=0.329, $\mu_s$=27.9 cm$^{-1}$, d=0.204 μm; (b) g=0.663, $\mu_s$=26.2 cm$^{-1}$, d=0.304 μm; (c) g=0.821, $\mu_s$=24.9 cm$^{-1}$, d=0.497 μm.

It was also found that $r_p$ depends on the anisotropy factor, g, of the particles in the suspensions. Results of measurements with crossed polarizers on three suspensions with similar scattering coefficients, $\mu_s$, but different g values are displayed in FIG. 10. The anisotropy factor, g, increases from g=0.329 (FIG. 10(a)) to g=0.663 (FIG. 10(b)) to g=0.821 (FIG. 10(c)). A comparison of the three figures shows that with increasing g the radius of the pattern increases.

Figure 11:
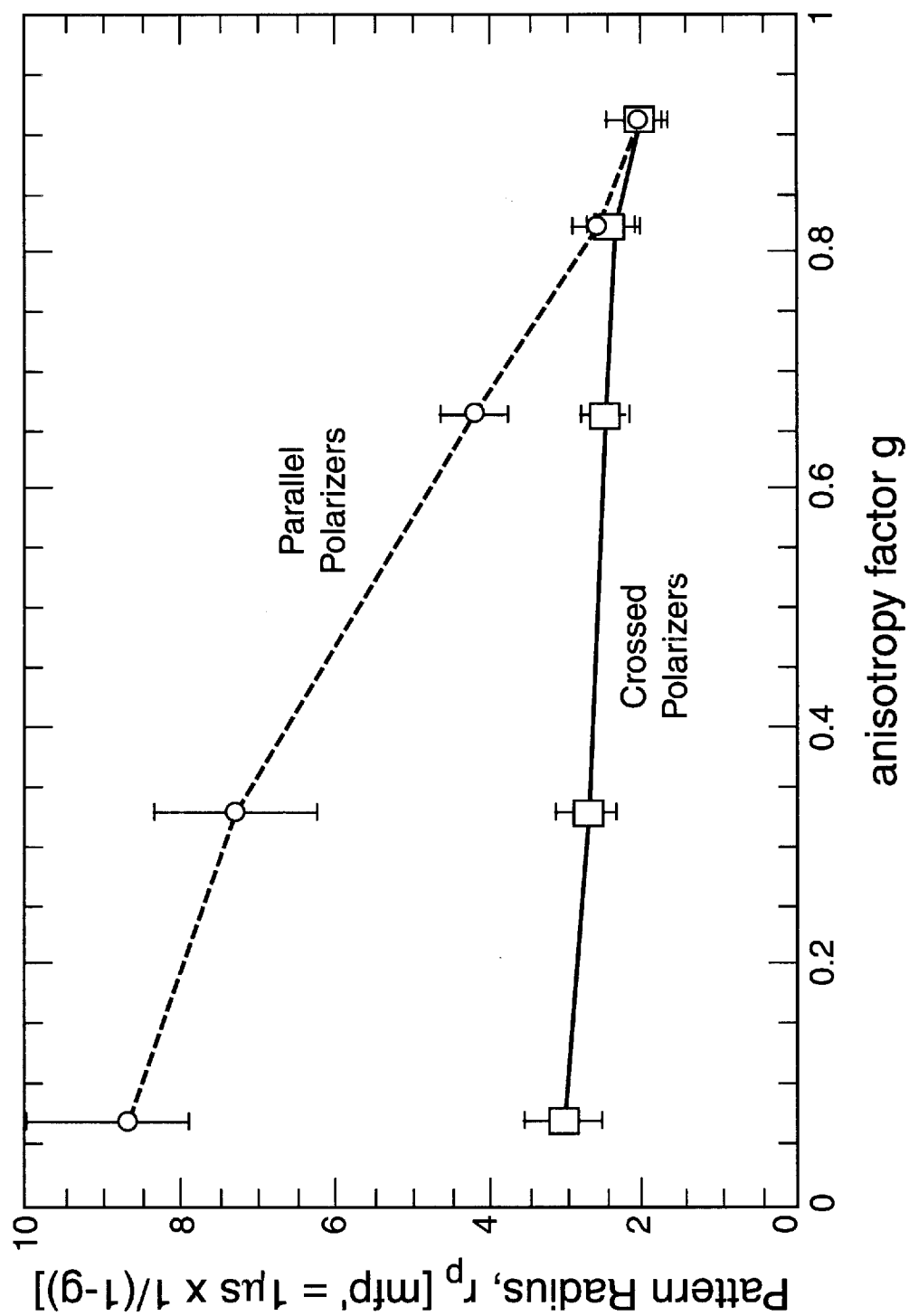
FIG. 11 shows the radius of the polarization pattern and its dependence on the anisotropy factor g for the cases if crossed polarizers (open squares, solid curve) and parallel polarizers (filled circles, dashed curve).

In FIG. 11 the radii of the patterns for crossed and parallel polarizers are displayed as functions of the g value. As units for $r_p$, the transport mfp, mfp'=$((1-g)\mu_s)^{-1}$ was chosen. Given these units, $r_p$ depends weakly on g for the case of crossed polarizers. A much stronger dependence on g can be observed for the case of parallel polarizers. For decreasing g values the parallel pattern increasingly exceeds the size of the crossed pattern, while for increasing g values the pattern sizes approach each other. If g=1, the unit mfp' becomes infinite and therefore $r_p$ should become 0 for both the parallel and crossed polarizer cases. Furthermore, it should be noted that using a different definition for the pattern radius, $r_p$, will shift these curve slightly; however, it does not change the overall dependence of $r_p$ on g.

Thus, by measuring the radius of the polarization pattern for crossed and parallel polarizers, $\mu_s$ and g of a turbid suspension can be estimated for a given index of refraction and wavelength. The ratio of the radii of the images taken with parallel and crossed polarizers yields a value for g. From FIG. 11 and the measurement of the radius of the crossed or parallel pattern, $\mu_s$ can be determined. Furthermore, as discussed hereinabove, the image with the parallel polarizer yields information about the diameter, d, of the particle responsible for the scattering.

Figure 12A:
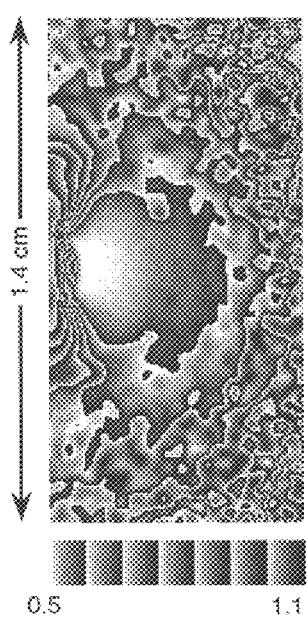
FIG. 12 shows the intensity ratio $I_{p,t}(r,\alpha)$ obtained from a 0.8% Intralipid solution with parallel polarizers: (a) two-dimensional image, (b) one-dimensional graph with radius fixed at $r=r_p/3$=0.15 cm. In both cases $0 \leq \alpha \leq 180°$.
Figure 12B:
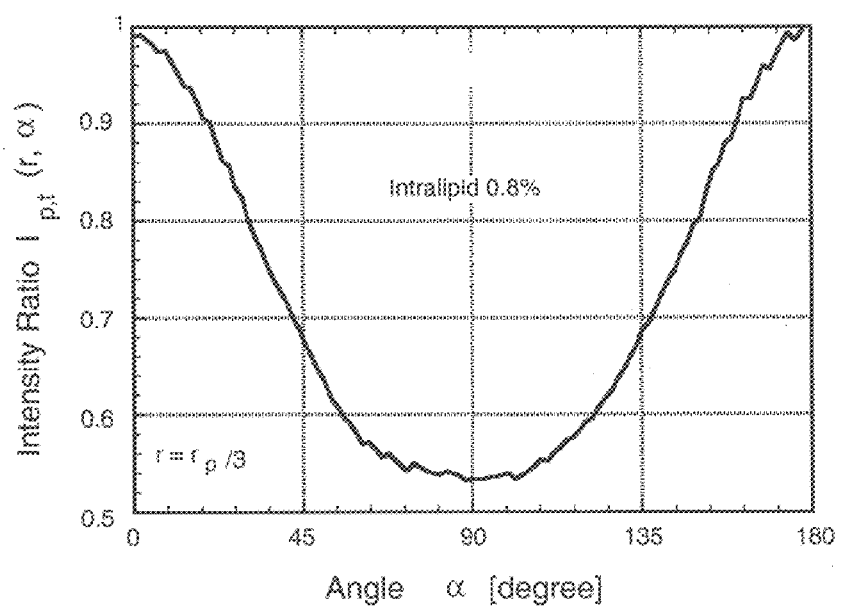

To determine if these patterns are observable in suspensions with a range of particle sizes, Intralipid solutions were investigated. In FIG. 12(a) the intensity ratio $I_{p,t}(r, \alpha)$ is shown for a 0.8% Intralipid suspension. FIG. 12(b) shows the azimuthal variation of $I_{p,t}$ for r=$r_p$/3=0.15 cm. When FIGS. 12(a) and 12(b) are compared with FIGS. 5(d) and 7, it can be seen that the polarization intensity pattern from the Intralipid suspension is similar to that observed with the polystyrene-sphere suspension with a particle diameter of 96 nm. The mean particle diameter in the Intralipid suspension is 97 nm. The ratio between the intensities at 90° and 0° of the Intralipid suspension yields 0.53 (FIG. 12(b)); using the polystyrene-sphere calibration curve (FIG. 8), this corresponds to a particle diameter of 110 nm (±20 nm). The pattern structure observed with mixed-size suspensions is approximated by the pattern observed with a single-size suspension, in which the particles have a diameter similar to the mean diameter of the mixed-size suspensions.

Other optical parameters of the suspension can be estimated as follows: The ratio, $R_{x,p}$, of the crossed pattern radius, $r_{p,x}$, divided by the parallel pattern radius, $r_{p,p}$, is $R_{x,p}=(r_{p,x})/(r_{p,p})=0.75$. From FIG. 11 it may be observed that if $R_{x,p}=0.75$, the anisotropy factor, g, is ~0.76. Furthermore, FIG. 11 shows that if g=0.76, the radius of the parallel pattern is approximately $r_{p,p}$=3.2 mfp'. From FIG. 12(a) the radius of the parallel pattern is measured to be $r_{p,p}$=0.45 cm and $$r_{p,p}=0.45 \text{ cm}=3.2 \text{ mfp'}=3.2 ((1-g)\mu_s)^{-1} \rightarrow \mu_s=29.6 \text{ cm}^{-1}.$$

These values for g and $\mu_s$ for a 0.8% Intralipid suspension, measured at the wavelength of λ=632.8 nm, lie within the range of values previously found in other studies.

Figure 13A:
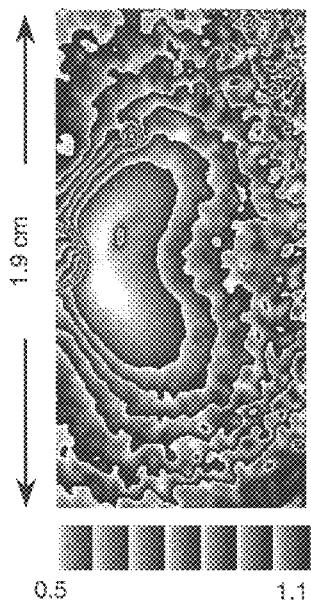
FIG. 13 shows the Intensity ratio, $I_{p,t}(r, \alpha)$, obtained from a wild-type yeast cell suspension (50 mg dry weight/ml) with parallel polarizers: (a) two-dimensional image, (b) one-dimensional graph with radius fixed at $r=r_p/3$=0.38. In both cases $0 \leq \alpha \leq 180°$.
Figure 13B:
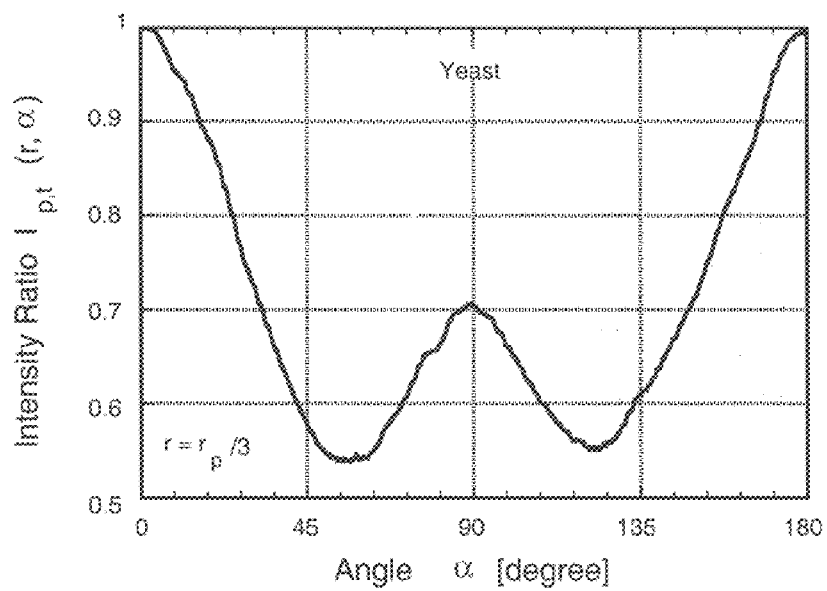

As an example of biological material, wild-type yeast cell suspensions were investigated. In FIGS. 3a–3c images for the crossed polarizers case were shown. FIG. 13(a) shows the related intensity ratio for parallel polarizers, and FIG. 13(b) displays the azimuthal variations for r=$r_p$/3=0.38 cm. When FIGS. 13(a) and 13(b) are compared with FIGS. 5(e) and 7, it is observed that the polarization intensity pattern from the yeast-cell suspension is similar to that observed with the polystyrene-sphere suspension with a particle diameter of 497 nm. The ratio between the intensities at 90° and 0° of the yeast-cell suspension yields 0.70; using the polystyrene-sphere calibration curve (FIG. 8), this corresponds to a particle diameter of 600 nm (±70 nm). Analysis for this yeast suspension (50 mg dry weight)/ml)) yields an anisotropy factor of approximately g=0.8 and a scattering coefficient of $\mu_s$=23.0 cm$^{-1}$.

The yeast cells had diameters in the range of approximately 3–8 $\mu$m (mean diameter 5.2 $\mu$m, SD=0.3 $\mu$m (5.8%)). Thus, the cell volume cannot be responsible for the major portion of the scattering. Smaller cell compartments like the nucleus, with a diameter of ~1 $\mu$m, or yeast-cell mitochondria, with a diameter of 0.2–0.5 $\mu$m, are likely to be the cause the light scattering.

FIG. 14(a) shows the intensity ratio, $I_{p,r}(r, \alpha)$, for the diffuse backscattering of polarized light from M1 rat fibroblast-cell suspensions for parallel polarizers. FIG. 14(b) displays the azimuthal variations for r=$r_p$/3=0.68 cm. The ratio between the intensities at 90° and 0° of the fibroblast-cell suspension is 0.555; using the polystyrene-sphere calibration curve (FIG. 8), this corresponds to a particle diameter of 200 nm (±40 nm). The mean diameter of the cells in this particular suspension is 15.2 $\mu$m (SD 1.2 $\mu$m (7.9%)). The largest cell observed had a diameter, d=2.3 $\mu$m, whereas the smallest cell had a diameter, d=8.4 $\mu$m. Therefore, it appears that the scattering is caused by much smaller structures. Fibroblast mitochondria with diameters of 0.05–0.3 $\mu$m seem to be the most likely source. Using near-infrared, time-resolved spectroscopy to probe rat liver mitochondria and liver-cell suspensions, Beauvoit et al. conclude that the light scattering from liver cells lies totally in its mitochondria content. See, e.g., B. Beauvoit et al., "Contribution of the Mitochondrial Compartment to the Optical Properties of the Rat Liver: A Theoretical and Practical Approach," Biophys. J. 67, 2501 (1994).

By probing a turbid medium with a narrow beam of linearly polarized light and viewing the diffuse-backscattered light with crossed and parallel polarizers, azimuthal and radial variations in the intensity around the light input point are observed. Studies with polystyrene-sphere suspensions reveal that, for a given wavelength and refractive index, the structures of these spatially varying intensity patterns depend on particle size, the anisotropy factor, g, and the scattering coefficient, $\mu_s$. The particle diameter can be deduced from the azimuthal variations of the pattern, and $\mu_s$ and g can be determined from the radial extent of the pattern. Experiments with Intralipid, yeast-cell, and fibroblast suspensions demonstrate that these patterns can also be observed in media that contain scattering centers with a range of sizes. The measurements on yeast cells and mammalian fibroblast cells suggest that particles much smaller than the cell volume, possibly mitochondria, cause most of the light scattering. Differences in mitochondria size and concentration are often observed between healthy and diseased cells and tissues.

EXAMPLE 2

In this example, the use of diffusely backscattered polarized light from biological material and other highly scattering media is generalized to include measurements of circularly polarized light and the introduction of the Mueller-matrix concept. While the Mueller matrix is well known to describe many optical elements and materials, matrix elements have not been obtained for diffusely backscattered light from turbid media. The matrix elements for various cancerous and noncancerous cell suspensions are compared with polystyrene-sphere suspensions. In particular, it is demonstrated that cancerous rat fibroblast cells, MRI, can be distinguished from noncancerous cells, M1, by measuring back-reflected circularly polarized light according to the teachings of the present invention.

The apparatus for studying the diffuse back-reflectance of polarized light is depicted as similar to that shown in FIG. 2 hereof, except that He-Ne laser 12 has an output power of 5 mW at a wavelength of $\lambda$=543 nm. Circularly polarized light is generated by inserting $\lambda$/4 mica retardation plate, 46, behind linear polarizer 14, with the retarder principle plane at ±45° with respect to the electric field vector of the incident linearly polarized light beam.

Two fibroblast suspensions were used to study diffuse back-reflection from biological material, all originating from the same rat-embryo-fibroblast cell line. A myc-gen mutation is induced to obtain M1 cells. A ras-gen mutation in addition to the mycgen gene leads to MR1 cells. Only the MR1 cells form a tumor if reinjected into a rat. See, e.g., L. A. Kunz-Schugart et al., "Three-Dimensional Cell Culture Induces Novel Proliferative and Metabolic Alterations Associated with Oncogenic Transformation," Int. J. Cancer 66, 578 (1996). A detailed description of the cell preparation is found in Hielscher et al., supra, and Andreas Hielscher et al., "Diffuse Backscattering Mueller Matrices For Highly Scattering Media," Optics Express 1, 441 (1997), the teachings of both references hereby being incorporated by reference herein. The two cell suspensions contained about $10^8$ cells/cm$^3$. Approximately 30 ml of each suspension was used for the backscattering experiments. To obtain the backscattered intensity images, the suspensions were placed in a cylindrical beaker with a diameter of 4 cm. The depth of the suspensions was approximately 2.5 cm.

Results obtained from the biological-cell suspensions were compared with aqueous polystyrene-sphere suspensions where spheres having diameters 204 nm, 497 nm, 890 nm, and 2040 nm were separately suspended in deionized water with trace amounts of surfactants. Particle concentrations resulted in reduced scattering coefficients, $\mu_s'=(1-g)\mu_s$, in the range of 1.8 to 2.2 cm$^{-1}$, which are comparable to values found for the cell suspensions.

A large number of experiments are possible for studying the polarization-dependent scattering properties of turbid media. The probing light may be linearly polarized at various angles, right-hand circularly, or elliptically polarized. Light emerging from the scattering medium can be analyzed in numerous ways as well. However, only a few measurements are needed to completely characterize the optical properties of any material. The necessary procedure is demonstrated by the Stokes-vector Mueller-matrix approach to polarization and light scattering as follows:

Each light beam can be represented by its four-component Stokes vector, S=(I,Q,U,V). The components of the Stokes vector are related to the electric field vectors as follows: 
$$S = \begin{bmatrix} I \\ Q \\ U \\ V \end{bmatrix} = \begin{bmatrix} \langle E_h E_h^* + E_v E_v^* \rangle \\ \langle E_h E_h^* - E_v E_v^* \rangle \\ \langle E_h E_v^* + E_v E_h^* \rangle \\ \langle i(E_h E_v^* - E_v E_h^*) \rangle \end{bmatrix}, \quad (3)$$

where $E_h$ and $E_v$ are electric field components horizontal and vertical with respect to the direction of light travel. The "*" indicates the complex conjugate, and the brackets represent time averages over time periods longer than T=1/f, where f is the optical frequency (~$10^{15}$/s). Some of the Stokes components are readily interpreted. For example, I=<$E_h E_h^* + E_v E_v^*$> is the time average of the sum of the products of the E-field amplitudes, which is equal to the total intensity. Examples for the Stokes vector notation are unpolarized light: [1,0,0,0], horizontal linearly polarized light: [1,1,0,0], vertical linearly polarized light: [1,−1,0,0], right-hand circular polarized light: [1,0,0,1], and left-hand circular polarized light: [1,0,0,−1].

In general, the interaction of light with optical elements such as lenses, polarizers, filters, surfaces, scattering media etc., changes the polarization state of the light from S to S'. When light is described by a four-component vector, this interaction with any optical element or material can be described as a multiplication of the Stokes vector with a 4×4 matrix S'=MS. This sixteen-element matrix is called the Mueller matrix or, if scattering is involved, the scattering matrix:

$$M = \begin{bmatrix} M_{11} & M_{12} & M_{13} & M_{14} \\ M_{21} & M_{22} & M_{23} & M_{24} \\ M_{31} & M_{32} & M_{33} & M_{34} \\ M_{41} & M_{42} & M_{43} & M_{44} \end{bmatrix}. \quad (4)$$

This matrix completely characterizes any component or material in terms of its optical properties. For example, a linear polarizer is described by $M_{11}=M_{12}=M_{21}=M_{22}=1$ and all other elements equal to zero. A right-hand circular polarizer is represented by $M_{11}=M_{14}=M_{41}=M_{44}=1$, and all other elements equal to zero.

Since the photograph of the surface around the laser input point represents diffusely backscattered light from turbid media (See FIGS. 1 and 2), rather than being a single number, each of the sixteen elements of the scattering matrix is a 2D array of numbers referring to different spatial locations on the surface of the medium.

Figure 15:
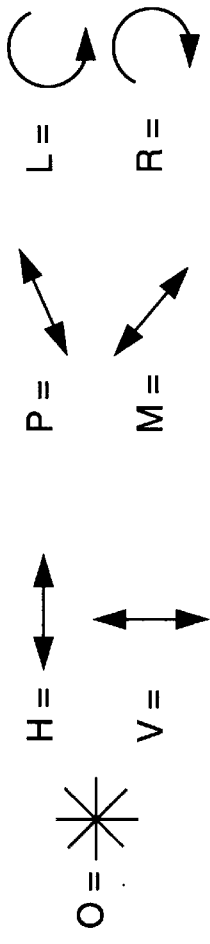
FIG. 15 is a list of the necessary measurements for each matrix element for the Mueller matrix.

If the Mueller matrix is not known, all the elements can be determined experimentally. It can be shown that 49 intensity measurements with various orientations of polarizers and analyzers are necessary to obtain the 16 elements of the Mueller matrix. See, e.g., W. S. Bickel et al., "Stokes Vectors, Mueller Matrices, and Polarized Scattered Light," Am. J. Phys. 53, 468 (1985). FIG. 15 lists the necessary intensity measurements for each matrix element. For example, to obtain the $M_{11}$ element one needs to measure the total reflected intensity from an unpolarized incident beam. The $M_{12}$ element is obtained by measuring the total reflected intensity for a horizontally, linearly polarized incoming beam and subtracting from this the total reflected intensity for a vertically, linearly polarized incident beam. More specifically, a two-letter combination stands for one measurement. For example, the combination (HV) means that the incoming light is linearly polarized along the horizontal axis (x-axis, see FIG. 3) and the analyzer is set to transmit light that is linearly polarized along the vertical axis (y-axis). To calculate $M_{22}$ four measurements are necessary: (HH), (VV), (HV) and (VH). "O" designates unpolarized light.

Figure 16:
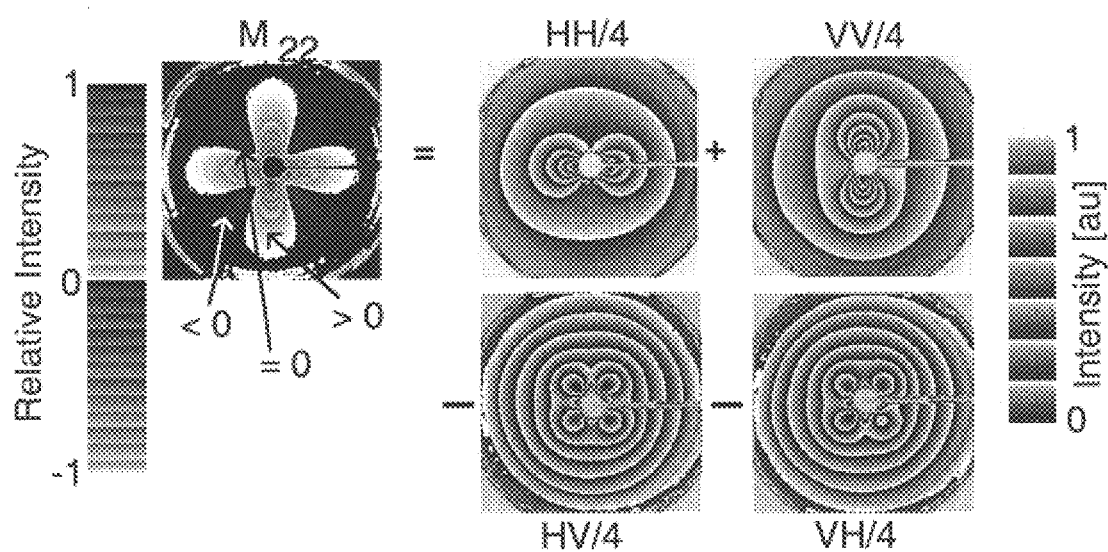
FIG. 16 shows a graphical depiction of the calculation of the $M_{22}$ element.

FIG. 16 is a graphical depiction of the calculation of the $M_{22}$ element from images obtained for suspensions of polystyrene spheres having a diameter of 204 nm at a concentration of 0.05% by weight. The scattering coefficient of the suspension was calculated to be $\mu'=1.9$ cm$^{-1}$. The intensity of the pattern located under the $M_{22}$ element may be understood by using the accompanying relative intensity scale and observing the regions marked greater than or less than zero, and their separation location marked zero. FIGS. 17, 18, 20 and 21 may be interpreted in a similar manner. Once all 16 elements of the matrix are obtained, the medium is completely described in terms of its optical characteristics. Thus, given any state of polarization of the incident beam, it is possible to calculate the state of polarization (Stokes vector) of the diffusely backscattered light. For example, if the incident beam is linearly polarized along the x-axis, the Stokes vector is given by S=[1,1,0,0]. This vector is multiplied by the Mueller matrix, M, to calculate the Stokes vector of the diffusely backscattered light. The light encounters an analyzer consisting of a linear polarizer along the y-axis, with $M_{11}=M_{22}=1$ and $M_{21}=M_{12}=-1$ and all other elements equal to 0. Thus, $$\begin{bmatrix} I \\ Q \\ U \\ V \end{bmatrix} = \begin{bmatrix} 1 & -1 & 0 & 0 \\ -1 & 1 & 0 & 0 \\ 0 & 0 & 0 & 0 \\ 0 & 0 & 0 & 0 \end{bmatrix} \cdot \begin{bmatrix} M_{11} & M_{12} & M_{13} & M_{14} \\ M_{21} & M_{22} & M_{23} & M_{24} \\ M_{31} & M_{32} & M_{33} & M_{34} \\ M_{41} & M_{42} & M_{43} & M_{44} \end{bmatrix} \cdot \begin{bmatrix} 1 \\ 1 \\ 0 \\ 0 \end{bmatrix} \quad (5)$$

$$= \begin{bmatrix} M_{11} + M_{12} - M_{21} - M_{22} \\ -M_{11} - M_{12} + M_{21} + M_{22} \\ 0 \\ 0 \end{bmatrix}.$$

As mentioned hereinabove, the first component, I, of the Stokes vector is equal to the total intensity which is the parameter measured with the apparatus of FIGS. 2a or 2b hereof. Therefore, the measured intensity will equal the sum of the four Mueller matrix elements $M_{11}+M_{12}-M_{21}-M_{22}$, of which $M_{22}$ for a 204-nm-sphere suspension is displayed in FIG. 4.

It should be noted that the measurement of the $M_{11}$ element, which is obtained without using polarizing optics in the apparatus, is known in the literature as "video-reflectometry". One can determine $\mu_s'$ and $\mu_s$ for a medium by analyzing the intensity decay as a function of r, the distance from the laser entry point into the medium. If $M_{11}$, does not depend on the azimuthal angle α, (see FIG. 3a), it is possible to measure the intensity decay as a function of r in a single dimension, rather than taking a two-dimensional image of the surface intensities. This method, often referred to as spatially resolved diffuse-reflectance measurement, has been used by many authors to determine optical properties of tissue phantoms and biological tissues. See, e.g., S. L. Jacques et al., "Video Reflectometry to Specify Optical Properties of Tissue in vivo," in *Medical Optical Tomography: Functional Imaging and Monitoring*, G. Mueller et al., eds., Vol. ISII of SPIE Institute Series (Society of Photo-Optical Instrumentation Engineers, Bellingham, Wash., 1992) pp. 211, A. Kienle et al., "Spatially Resolved Absolute Diffuse Reflectance Measurements for Noninvasive Determination of the Optical Scattering and Absorption Coefficients of Biological Tissue," Appl. Opt. 35, 2304 (1996), and T. J. Farrell et al., supra.

The introduction of the Mueller-matrix concept to the analysis of diffusely backscattered light provides, in addition to the widely used $M_{11}$ element, 15 additional elements, which can be evaluated to obtain further information about scattering media. Because the description of the optical characteristics of a medium using the Mueller matrix is complete, any information about particle size, refractive index, particle shape, etc. is to be found in the Mueller matrix by analysis of the matrix elements. If some information about the medium cannot be extracted from the various matrix elements, this information cannot be extracted from further backscattering measurements. However, additional information about the medium may be obtained, for example, by measuring the diffuse transmittance, the diffuse back-reflectance at different incident and observation angles, or time-dependent polarization effects.

Figure 17:
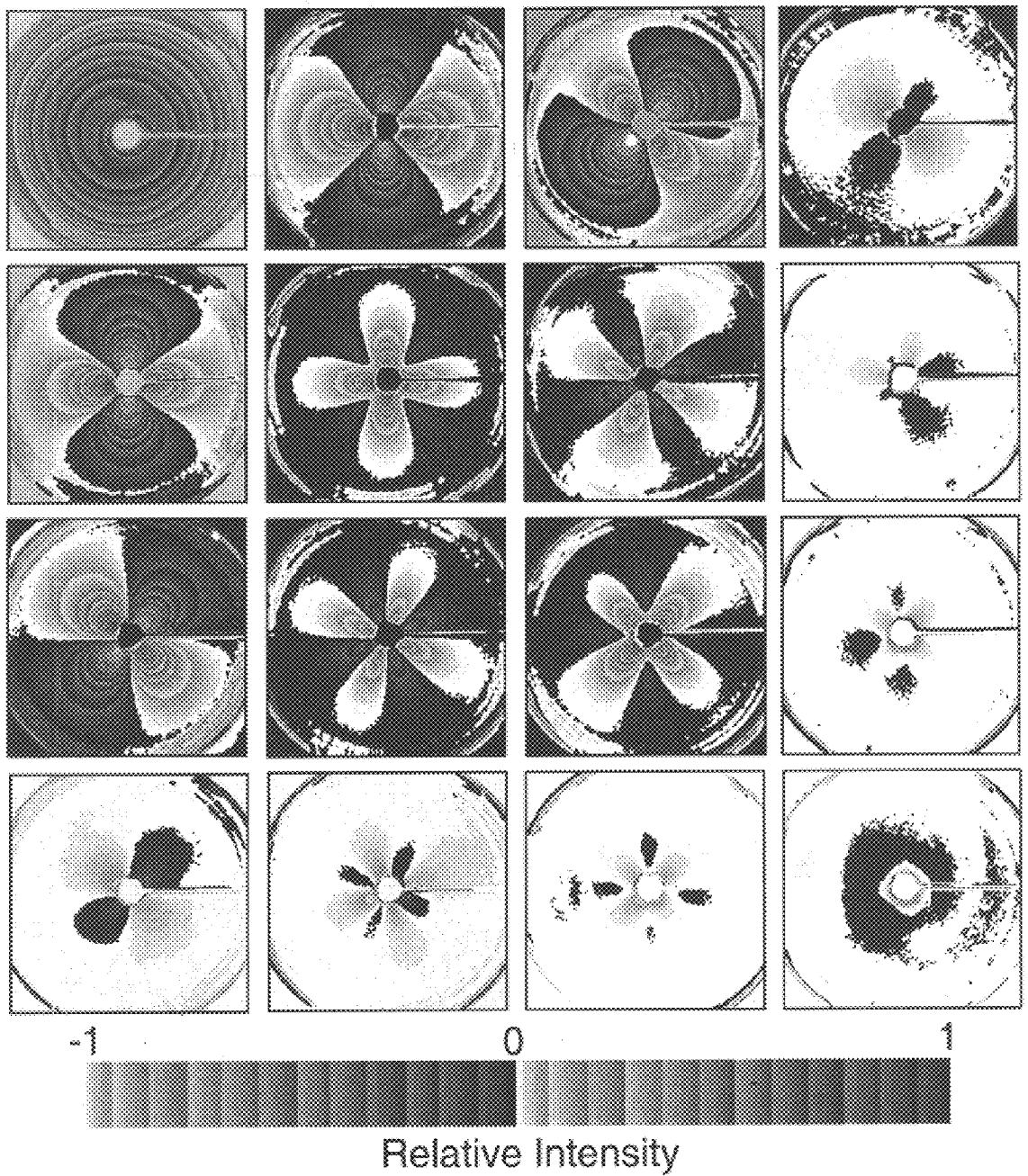
FIG. 17 shows the diffuse backscattering Mueller matrix elements for a polystyrene-sphere suspension with mono-disperse particle diameter of d=204 nm ($\mu_s'$=1.9 cm$^{-1}$). The upper left corner is $M_{11}$, the lower right corner is $M_{44}$ (see Eq. 4 and FIG. 15). The scale is normalized so that the maximum intensity of the $M_{11}$ element equals 1. All images displayed are 3.5 cm×3.5 cm.

FIG. 17 shows all 16 Mueller matrix elements obtained for a polystyrene-sphere suspension with particles of 204 nm diameter. The particle concentration is 0.05% by weight, which results in a reduced scattering coefficient of $\mu_s'=1.9$ cm$^{-1}$. The displayed intensities are relative to the maximum intensity of the $M_{11}$ element. This element is always positive; however, all other elements can have negative values because different intensity measurements are subtracted from each other (See FIG. 16).

Several observations can be made: First, $M_{nm}=M_{mn}$, which means that this Mueller matrix is symmetric. The difference between the measurement of $M_{mn}$ and of $M_{nm}$ is that the polarization optics before and after the medium are exchanged (see FIG. 2, first and second polarization elements). Therefore, if the scattering medium is not optically active and has no internal structure that results in some preferred optical axis, $M_{nm}$ must equal $M_{mn}$. Furthermore, several pairs of elements exist that differ only in the orientation of the intensity pattern. For example, $M_{13}$ can be obtained by rotating $M_{12}$ by 45°. The same relation holds for the pairs $M_{31}$ and $M_{21}$, and $M_{22}$ and $M_{33}$. The only difference between the measurements of these pairs is a rotation of the polarization and analyzer optics (first and second polarizers of FIGS. 2a and 2b) by 45°. Finally, the elements in the last column ($M_{14}$, $M_{24}$, $M_{34}$, $M_{44}$) and the last row ($M_{41}$, $M_{42}$, $M_{43}$, $M_{44}$) are approximately zero, while all other elements show strong azimuthal variations in the relative intensity.

Figure 18:
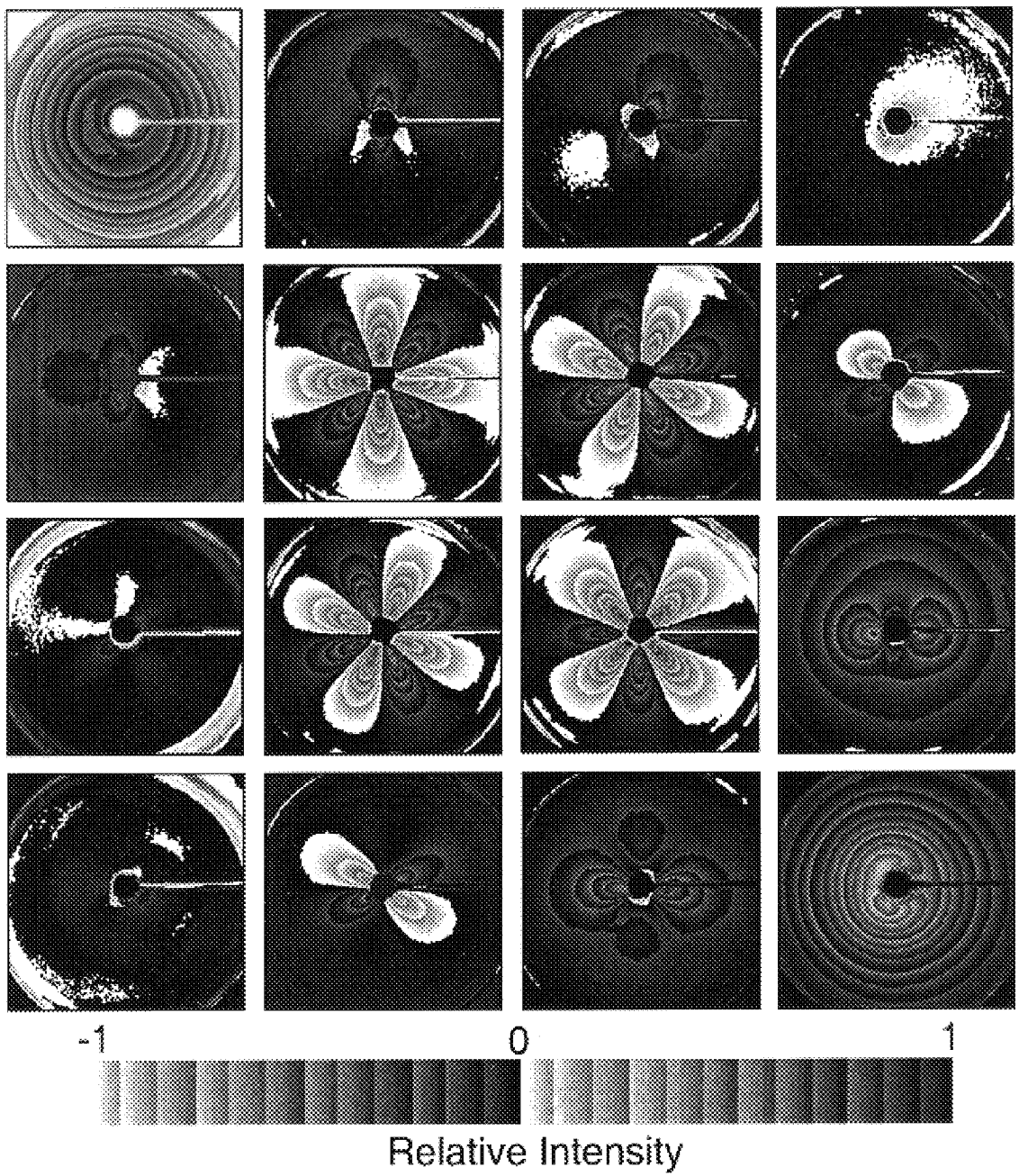
FIG. 18 shows the diffuse backscattering Mueller matrix elements for a polystyrene-sphere suspension with mono-disperse particle diameter of d=2040 nm (with $\mu_s'$=1.9 cm$^{-1}$). All images displayed are 3.5 cm×3.5 cm.

When the 204-nm-particle suspension of FIG. 17 is compared to a suspension of 2040-nm-diameter spheres ($\mu_s'=1.9$ cm$^{-1}$) in FIG. 18, the last row and last column show azimuthal intensity variations, while the first row and first column ($M_{12}$, $M_{13}$, $M_{14}$, and $M_{21}$, $M_{31}$, $M_{41}$) are approximately zero. Other differences are the more pronounced azimuthal variation of the center elements $M_{22}$, $M_{32}$, $M_{23}$, and $M_{33}$. The matrix symmetries are the same as for the 204-nm sphere suspensions. Also, since the reduced scattering coefficients of the two suspensions are identical, the $M_{11}$ elements are the same. (The radial intensity decay only depends on $\mu_s'$ and $\mu_a$, and $\mu_a$ is negligible in both cases.) This demonstrates the advantages of the Mueller matrix approach over standard video reflectometry which is based on unpolarized light measurements. The addition of polarization properties permits 204-nm and 2040-nm sphere suspensions to be distinguished, even when the reduced scattering coefficients are the same.

All sixteen Mueller matrix components taken together provide a "finger print" of the scattering medium under investigation, and observing the entire Mueller matrix often enables two media to be qualitatively distinguished. To obtain a quantitative distinction between different media, more detailed analyses of single matrix elements are necessary. As an example, changes in the $M_{44}$ element as a function of particle diameter in monodisperse, polystyrene-sphere suspensions are investigated.

Figure 19:
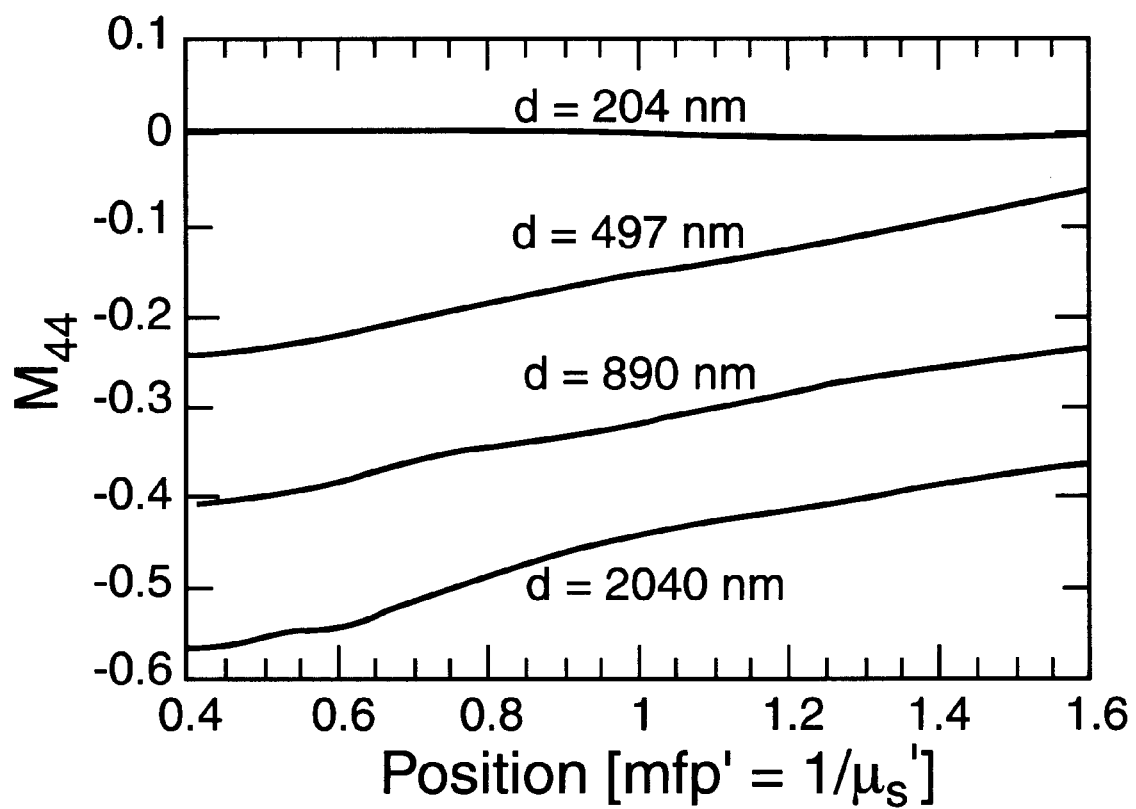
FIG. 19 shows the radial dependence of $M_{44}$ obtained from four different polystyrene-sphere suspensions. The numbers indicate the diameter, d, of the spheres in the suspension. The radial distance is given in units of transport mean free path (mfp').

The $M_{44}$ element is calculated from four measurements which involve only circularly polarized light (from FIG. 15, $M_{44}$=LL+RR−LR−RL). This element is a measure of how effectively a medium flips the helicity of the backscattered light. For a perfect mirror, the element $M_{44}$=−1 because perpendicular-incident, left-hand, circularly polarized light returns as right-hand circularly polarized light and vice a versa. (therefore, LL=RR=0 and LR=RL=1). In the case of the polystyrene-sphere suspension, $M_{44}$ has no azimuthal dependence. Therefore, the values of this element along the y-axes from the 2-dimensional images of $M_{44}$ are extracted. The results for four different sphere suspensions are shown in FIG. 19. It is seen that $M_{44}$ decreases with increasing sphere diameter. Therefore, the suspensions with larger spheres flip the helicity more effectively, and most of the backscattered light has a different helicity than the incident light. This behavior can be understood if one considers that with increasing diameter the spheres become more and more like a mirror, which can be thought of as a sphere with infinite radius. If the polystyrene spheres are small (d=204 nm) compared to the wavelength ($\lambda$=543 nm), the backscattered light is equally left-hand and right-hand polarized and the element is zero. Furthermore, the effect is strongest in the center near the laser entry point. Here the backscattered light has undergone only a few scattering events and the polarization effects are strongest. With increasing distance from the point of light incident, the number of scattering events increases and eventually the polarization information is lost, that is, the value of the $M_{44}$ approaches zero.

Figure 20:
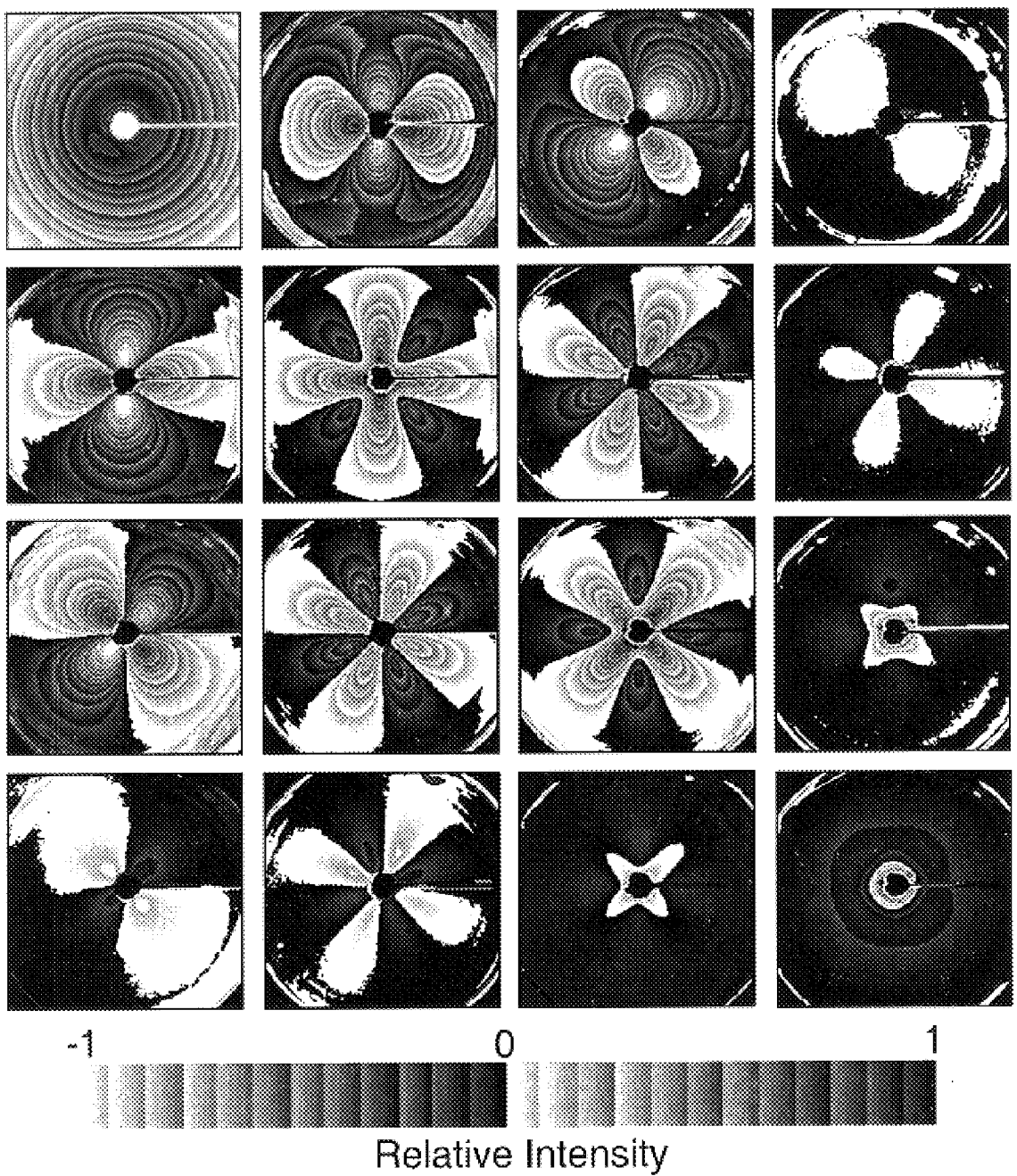
FIG. 20 shows the diffuse-backscattering Mueller matrix for a M1 cell suspension with $10^8$ cells/cm$^3$.
Figure 21:
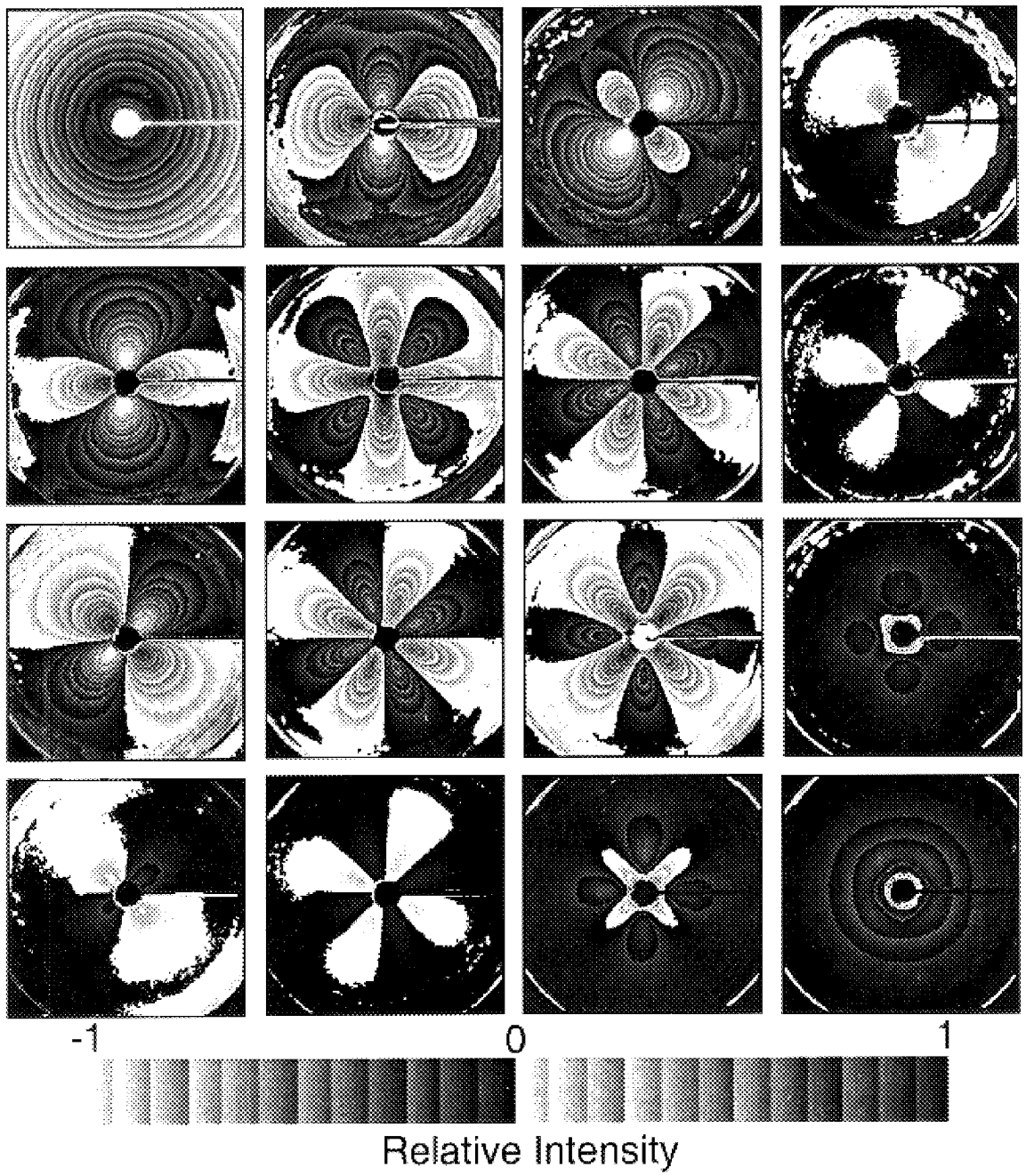
FIG. 21 shows the diffuse-backscattering Mueller matrix for a cancerous MR1 cell suspension with $10^8$ cells/cm$^3$.

In addition to monodisperse particle suspensions with known optical properties, we also applied the Mueller matrix approach to biological cell suspensions. FIGS. 20 and 21 show the results obtained for cancerous (MR1) and noncancerous (M1) rat fibroblast suspensions. Both suspensions contain $10^8$ cells/cm$^3$, and the scattering coefficient were $\mu_s'$=2.2 cm$^{-1}$ (±10%) and $\mu_s'$=2.1 cm$^{-1}$ (±10%) for the MR1 and M1 cells, respectively. The two matrixes are almost identical. Small differences are observed for the $M_{22}$ and $M_{33}$ elements. In these matrix elements the negative values close to the center appear slightly more pronounced. Larger differences between the tumorigenic MR1 cells and the nontumorigenic M1 cells can be seen in the $M_{44}$ elements.

Figure 22:
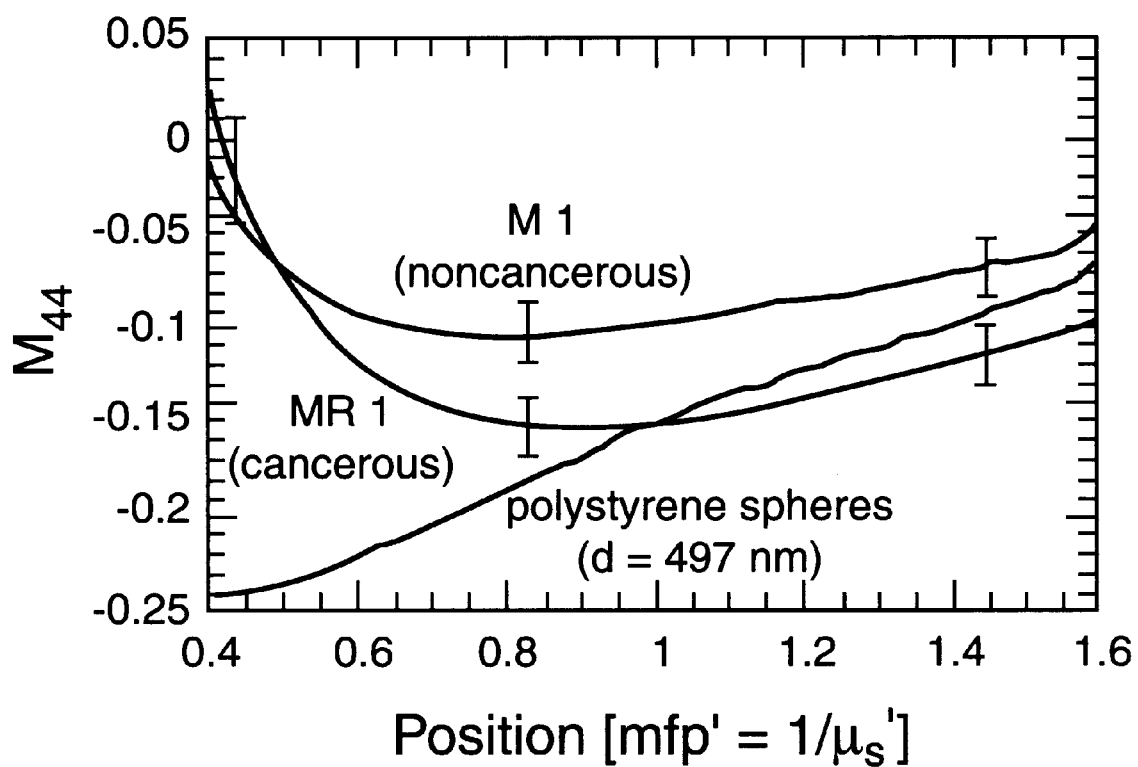
FIG. 22 shows the radial dependence of $M_{44}$ obtained from cell suspensions; as a reference the result for a 497-nm-polystyrene-sphere suspension is also shown (see FIG. 19).

The $M_{44}$ element is radially symmetric for the MR1 cells as well as the M1 cells. FIG. 22 shows the radial dependence along the y-axes of M44 for r=0.4 to 1.6 mfp' (mfp'= transport mean free path=1/$\mu_s'$). The laser light enters the medium at r=0 mfp'. Data for r<0.4 mfp' is omitted because this range is covered or distorted by the optical mask. For radial distances r>0.5 mfp', the $M_{44}$ element for the MR1 suspension is smaller. This means that in this range the cancerous cell suspension flips the helicity of the incident light more than the noncancerous cell suspension.

Comparing FIG. 22 with the results found for polystyrene-sphere suspensions in FIG. 19 for distances larger than 0.9 mfp' from the light input point, backscattering from the cell suspensions is similar to backscattering from 497-nm-sphere suspension. However, for smaller distances the value of the $M_{44}$ element for the polystyrene-sphere suspension decreases as the light incident point is approached, while the value of $M_{44}$ for the cell suspensions increases. The reason for this behavior is unclear. Possible explanations may be related to the nonspherical shapes of the scatterers within the cell, scattering contributions from particles with various sizes, or optical activity of the medium.

In summary an apparatus and method is described for the study of diffusely backscattered polarized light from highly scattering media. The present method is an extension of spatially resolved reflectometry and video reflectometry. These methods use unpolarized light in the study of optical properties ($\mu_s'$ and $\mu_a$) of turbid media. With the use of a polarized incident beam and the analysis of various polarization components in the diffusely backscattered light according to the teachings of the present invention, complex, 2-dimensional, spatially varying surface-intensity patterns are observed. These patterns can be used to gain additional information about the scattering medium and to distinguish between media with the same $\mu_s'$ and $\mu_a$.

An infinite number of different backscattering measurements using polarized light can be performed by varying the polarization state of the incident beam and detecting different polarization components of the diffusely backscattered light. However, by introducing the Stokes-vector, Mueller-matrix concept for diffusely backscattered light, subsets of measurements that comprehensively describe the optical properties of backscattering media may be selected. With 49 measurements, all 16 elements of the diffuse-backscattering Mueller matrix can be determined. Knowing all 16 elements of this matrix one can calculate the polarization state of the backscattered light given any polarization state of the incident light. Therefore, knowing all 16 elements completely describes the medium in terms of optical properties. Clear differences among different monodisperse polystyrene-sphere suspensions are observed in several matrix elements, even when the suspensions have the same scattering and absorption coefficients. Further, the $M_{44}$ element, which is obtained from measurements employing right and left-hand circularly polarized light, is especially sensitive to particle sizes in the suspension, and suspensions of cancerous and noncancerous rat fibroblast cells can be differentiated using the $M_{44}$ element.

In contrast to suspensions, tissues are highly structured and often have preferred optical axes. These structures should affect the elements of the Mueller matrix. Furthermore, tissues have, in general, a higher scattering coefficient than the suspensions described hereinabove, which means that polarization effects will be limited to a smaller distance from the laser incident point, and a microscope or fiber optics may be required to spatially resolve the patterns in the matrix elements.

The foregoing description of the invention has been presented for purposes of illustration and description and is not intended to be exhaustive or to limit the invention to the precise form disclosed, and obviously many modifications and variations are possible in light of the above teaching. For example, a white light source and optical filters may be used in place of a laser, and selected wavelengths may be chosen from the infrared region of the electromagnetic spectrum to the ultraviolet region thereof in order to obtain additional information from the samples under investigation. The bandwidth of the electromagnetic radiation in a chosen wavelength region must be such that polarization can be achieved by the polarization elements employed. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. Apparatus for measuring diffuse backscattering of electromagnetic radiation from a medium, which comprises in combination:

(a) a source of electromagnetic radiation having a chosen wavelength;

(b) first polarizer means for receiving the electromagnetic radiation and for selectively polarizing the electromagnetic radiation;

(c) means for directing the polarized electromagnetic radiation into a small area of the medium substantially perpendicular to the surface of the medium;

(d) means for collecting multiply-scattered electromagnetic radiation emerging from the medium in the vicinity of the area of entry of the electromagnetic radiation into the medium and in the opposite direction to the direction of the incident electromagnetic radiation;

(e) mask means for blocking specular reflection from the surface of the medium in the collected backward-scattered electromagnetic radiation;

(f) second polarizer means for receiving the collected backward-scattered electromagnetic radiation and for selectively polarization analyzing the collected backward-scattered electromagnetic radiation; and (g) means for receiving the polarization-analyzed, collected backward-scattered electromagnetic radiation and simultaneously recording the spatial components of the intensity thereof.

2. The apparatus as described in claim 1, further comprising lens means for varying the size of the region in the vicinity of the entry point of the electromagnetic radiation into the medium viewed by said recording means.

3. The apparatus as described in claim 1, wherein said source of electromagnetic radiation includes a source of visible light.

4. The apparatus as described in claim 3, wherein said source of visible light includes a helium-neon laser.

5. The apparatus as described in claim 1, wherein the selective polarization achieved by said first polarizer means and analyzed by said second polarization means is selected from the group consisting of linear polarization at various angles, right-hand circular polarization, left-hand circular polarization, and elliptical polarization.

6. A method for differentiating among samples of turbid media, which comprises the steps of:

(a) generating polarized electromagnetic radiation having selective polarization and a chosen wavelength;

(b) directing the polarized electromagnetic radiation into a small area of the turbid medium substantially perpendicular to the surface of the medium;

(c) collecting multiply-scattered electromagnetic radiation emerging from the medium in the vicinity of the area of entry of the electromagnetic radiation into the medium and in the opposite direction to the direction of the incident electromagnetic radiation;

(d) blocking specular reflection from the surface of the medium in the collected backward-scattered electromagnetic radiation;

(e) polarization analyzing the backward-scattered electromagnetic radiation; and (f) simultaneously recording the spatially resolved components of the intensity of the backward-scattered electromagnetic radiation for at least one combination of selected polarization and polarization analysis, whereby the recorded spatially resolved components of the intensity for different media are compared for said at least one combination of selected polarization and polarization analysis.

7. The method as described in claim 6, wherein the generated electromagnetic radiation includes visible light.

8. The method as described in claim 6, wherein the selective polarization is selected from the group consisting of linear polarization at various angles, right-hand circular polarization, left-hand circular polarization, and elliptical polarization.

9. The method as described in claim 6, wherein said step of polarization analyzing the backward-scattered electromagnetic radiation includes the use of generalized Mueller matrix analysis.

* * * * *